(12) United States Patent
Karin et al.

(10) Patent No.: US 9,717,777 B2
(45) Date of Patent: Aug. 1, 2017

(54) USE OF CCL1 IN THERAPY

(71) Applicant: RAPPAPORT FAMILY INSTITUTE FOR RESEARCH IN THE MEDICAL SCIENCES, Haifa (IL)

(72) Inventors: Nathan Karin, Haifa (IL); Yiftah Barsheshet, Kfar-Tavor (IL); Gizi Wildbaum, Kiryat Yam (IL)

(73) Assignee: RAPPAPORT FAMILY INSTITUTE FOR RESEARCH IN THE MEDICAL SCIENCES, Haifa (IL)

( * ) Notice: Subject to any disclaimer, the term of this patent is extended or adjusted under 35 U.S.C. 154(b) by 0 days.

(21) Appl. No.: 15/163,689

(22) Filed: May 25, 2016

(65) Prior Publication Data

US 2016/0303196 A1   Oct. 20, 2016

Related U.S. Application Data

(63) Continuation-in-part of application No. 13/696,093, filed as application No. PCT/IL2011/000361 on May 5, 2011, now Pat. No. 9,352,000.

(60) Provisional application No. 61/331,438, filed on May 5, 2010.

(51) Int. Cl.

| | |
|---|---|
| A61K 38/00 | (2006.01) |
| C07K 14/47 | (2006.01) |
| A61K 38/16 | (2006.01) |
| A61K 38/19 | (2006.01) |
| C07K 14/52 | (2006.01) |

(52) U.S. Cl.
CPC ............ *A61K 38/19* (2013.01); *A61K 38/16* (2013.01); *A61K 38/195* (2013.01); *C07K 14/521* (2013.01); *C07K 2319/30* (2013.01)

(58) Field of Classification Search
None
See application file for complete search history.

(56) References Cited

U.S. PATENT DOCUMENTS

2004/0191255 A1   9/2004   Lillard et al.
2009/0214533 A1   8/2009   Clynes

FOREIGN PATENT DOCUMENTS

| WO | WO 03/051921 | 6/2003 |
|---|---|---|
| WO | WO 2004/045525 | 6/2004 |
| WO | WO 2005/016962 | 2/2005 |
| WO | WO 2008/145142 | 12/2008 |
| WO | WO 2011/138785 | 11/2011 |
| WO | WO 2012/166588 | 12/2012 |

OTHER PUBLICATIONS

Whisstock et al. 2003 Quart. Rev. Biophys. vol. 36 pp. 307-340.
Vanderlugt, C.L. & Miller, S.D., Epitope spreading in immune-mediated diseases: implications for immunotherapy, Nature Reviews Immunology, vol. 2, pp. 85-95, 2002.
Pierson et al., Mechanisms regulating regional localization of inflammation during CNS autoimmunity, Immunology Reviews, vol. 248, pp. 205-215, 2012.
Codarri et al., L., ROR*gammat* drives production of the cytokine GM-CSF in helper T cells, which is essential for the effector phase of autoimmune neuroinflammation, Nature Immunology, vol. 12, 560-567, 2011.
Mix el al., Animal models of multiple sclerosis-Potentials and limitations, Progress in Neurobiology, vol. 92, pp. 386-404, 2010.
Powrie, F., T Cells in Inflammatory Bowel Disease: Protective and Pathogenic Roles. Immunity, vol. 3, pp. 171-174, Aug. 1995.
Feldmann et al., Rheumatoid arthritis. Cell, vol. 85, pp. 307-310, 1996.
Collison, L.W. & Vignali, D.A., In vitro Treg suppression assays, Methods in Molecular Biology 707, 21-37, 2011.
Fairweather and Cihakova, Alternatively activated macrophages in infection and autoimmunity, Journal of Autoimmunity, vol. 33, pp. 222-230, 2009.
Asai et al., CCL1 released from M2b macrophages is essentially required for the maintenance of their properties, Journal of Leukocyte Biology, vol. 92, pp. 859-867, Oct. 2012.
Butti et al. "IL4 Gene Delivery to the CNS Recruits Regulatory T Cells and Induces Clinical Recovery in Mouse Models of Multiple Sclerosis", Database Biosis [Online] Biosciences Information Service, Philadelphia, PA, US, Apr. 2008, XP002660971, & Gene Therapy, vol. 15, No. 7, pp. 504-515, Apr. 2008.
Gonzalo et al. "Coordinated Involvement of Mast Cells and T Cells in Allergic Mucosal Inflammation: Critical Role of the CC Chemokine Ligand 1: CCR8 Axis" Database Biosis [Online], Biosciences Information Service, Philadelphia, PA, US, Aug. 2007, XP002660972, & Journal of Immunology, vol. 179, No. 3, pp. 1740-1750, Aug. 2007.
Alvarado-Sanchez et al. "Regulatory T Cells in Patients with Systemic Lupus Erythematosus", Journal of Autoimmunity, 2006, vol. 27, pp. 110-118.
Broady et al. "Graft-Versus-Host Disease: Suppression by Statins", Nature Medicine, Nov. 2008, vol. 14, No. 11, pp. 1155-1156.
Cohen et al. "CD4+CD25+ Immunoregulatory T Cells New Therapeutics for Graft-Versus-Host Disease", Journal of Experimental Medicine, Aug. 5, 202, vol. 196, No. 3, pp. 401-406.
Hori et al. "Control of Regulatory T Cell Development by the Transcription Factor Foxp3", Science, Feb. 14, 2003, vol. 299 pp. 1057-1061.
Mira et al. "Statins Induce Regulatory T Cells Recruitment Via A CCL1 Dependent Pathway", The Journal of Immunology, 2008, vol. 181, pp. 3524-3534.

*Primary Examiner* — Amy Juedes
(74) *Attorney, Agent, or Firm* — Pearl Cohen Zedek Latzer Baratz LLP

(57) ABSTRACT

A method of treating a medical condition in which suppression of effector T cells is beneficial in a subject in need thereof is disclosed. The method comprising administering to the subject a therapeutically effective amount of a CCL1 polypeptide, thereby treating the medical condition in the subject.

3 Claims, 10 Drawing Sheets

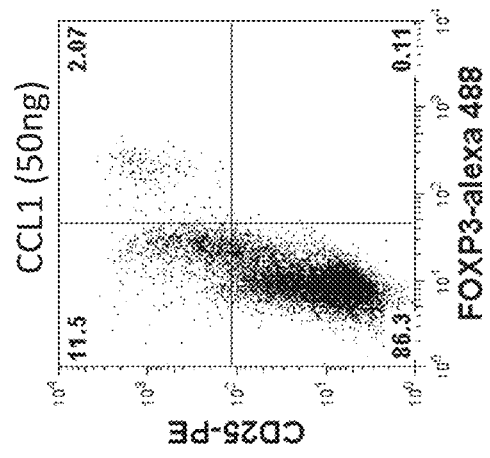
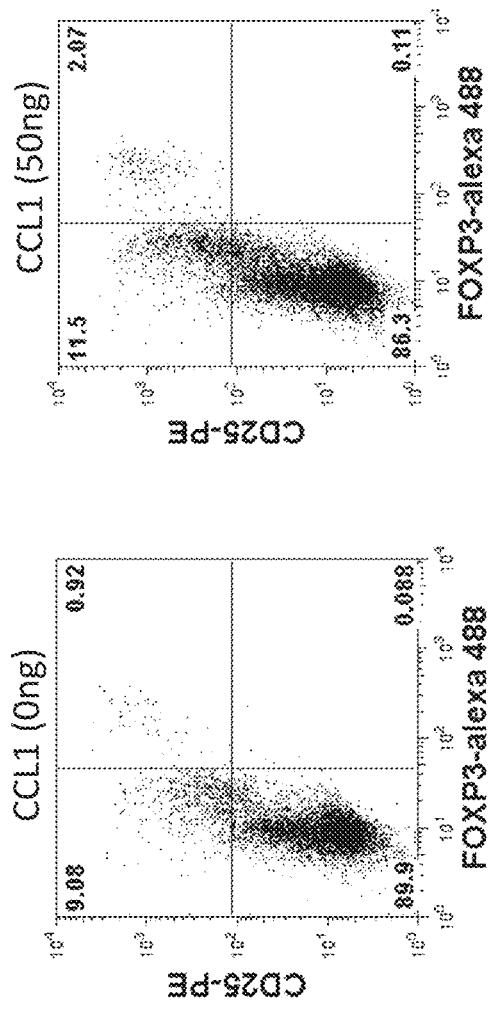
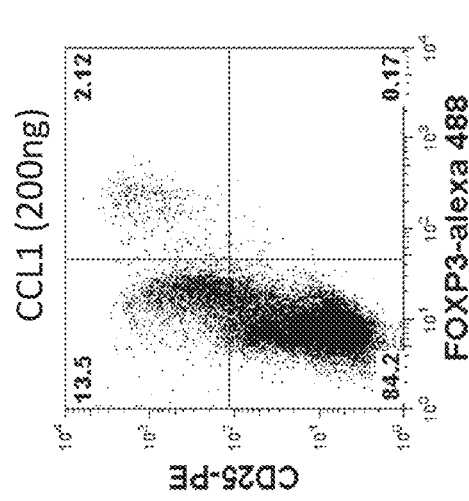

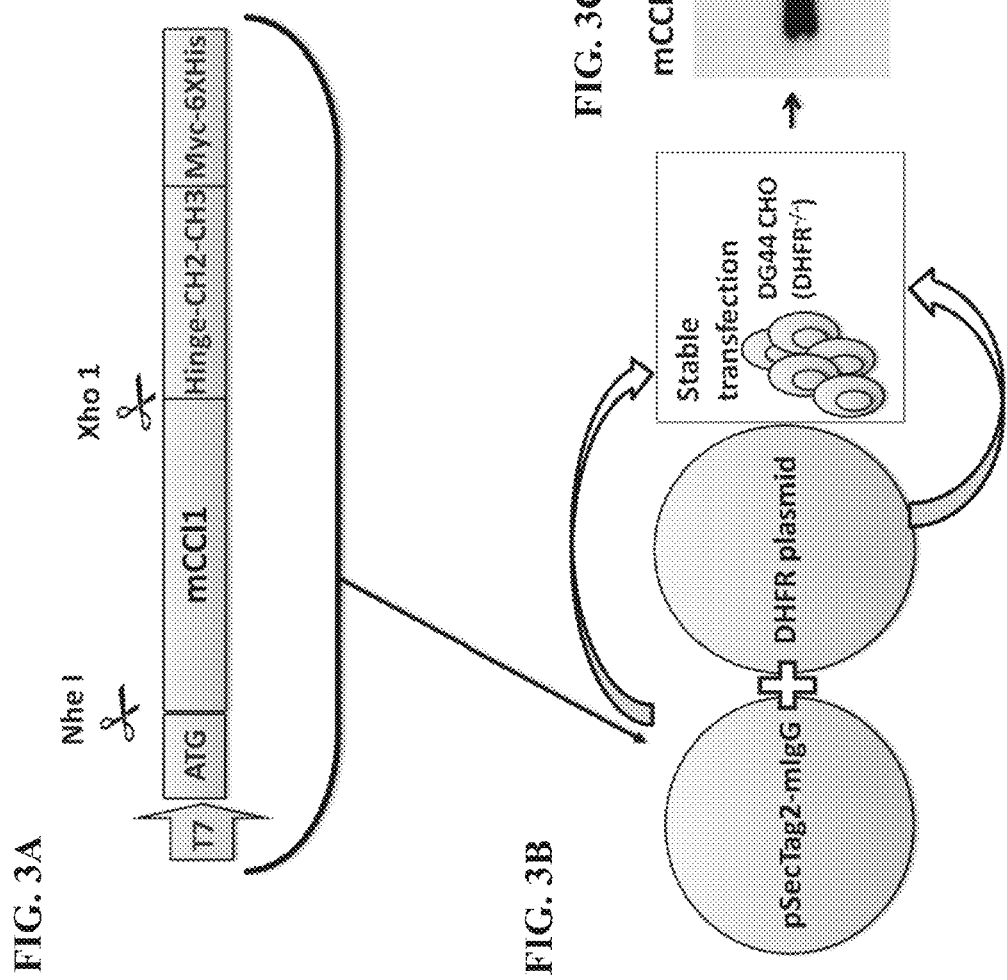

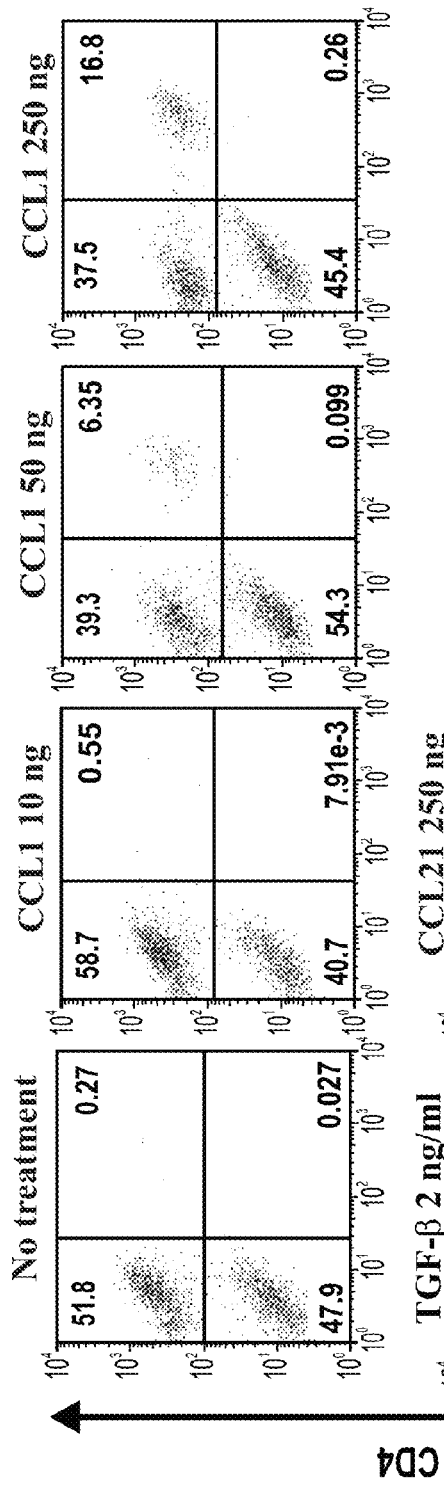

CCL1 ameliorates TNBS induced colitis in SJL mice

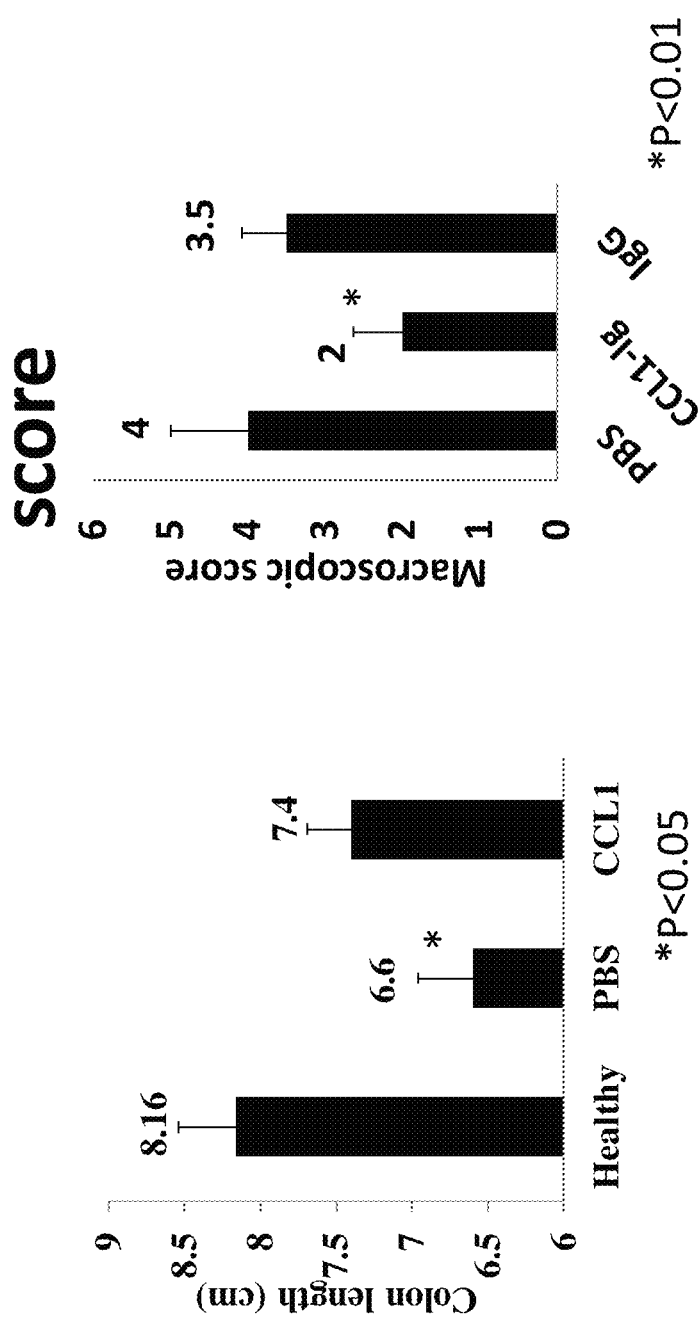

USE OF CCL1 IN THERAPY

RELATED APPLICATIONS

This application is a Continuation in Part of U.S. application Ser. No. 13/696,093, now U.S. Pat. No. 9,352,000 which in turn is the National Phase of PCT Patent Application No. PCT/IL2011/000361, having International filing date of May 5, 2011, which claims the benefit of priority under 35 USC §119(e) of U.S. Provisional Patent Application No. 61/331,438 filed on May 5, 2010. The entire contents of the above applications are all incorporated by reference, as if fully set forth herein.

FIELD AND BACKGROUND OF THE INVENTION

The present invention, in some embodiments thereof, relates to CCL1 molecules and, more particularly, but not exclusively, to the use of same for therapy, such as of inflammatory, autoimmune and transplantation-related diseases.

Graft-versus-host disease (GVHD) is a major complication of allogeneic bone marrow transplantation (BMT) leading to significant morbidity and mortality in humans. However, BMT is currently the preferred treatment of a number of malignant and non-malignant diseases, including acute and chronic leukemia, myelomas, lymphomas, aplastic anemia, solid tumors and severe immunodeficiency. Acute and chronic GVHD occurs when transplanted donor-derived T cells recognize and react to histo-incompatible recipient antigens (Ags) and/or cells. Acute GVHD typically occurs within 100 days of transplantation and is a rapidly progressive syndrome characterized by profound wasting, immunosuppression and tissue injury in a number of organs, including the intestines, spleen, skin, liver and lungs.

GVHD is considered to be an inflammatory process, with similarities to inflammatory autoimmunity. Yet, most anti-inflammatory therapies, including those showing success in human inflammatory autoimmunity failed in treating GVHD. For example, targeted neutralization of TNF-α by neutralizing antibodies or soluble receptor to TNF-α successfully suppresses rheumatoid arthritis and several other human inflammatory autoimmune diseases, but not GVHD.

Experimental autoimmune encephalomyelitis (EAE) is a CD4+ T cell mediated murine autoimmune disease that serves as an experimental model for Multiple Sclerosis (MS). EAE also serves as an experimental model for the development of anti-inflammatory therapeutic strategies for a variety of inflammatory autoimmune diseases and for inhibition of graft rejection. For example, studies showing that inhibition of the CTL-A-CD28 interaction is beneficial for therapy of EAE were extended to a variety of autoimmune diseases including, rheumatoid arthritis, atherosclerosis, myocarditis and also to inhibition of graft rejections.

A potential approach for therapy of inflammatory autoimmune and graft rejection encompasses induction of regulatory T cells (T-regs) that control the function of inflammatory effector T cells. The inflammatory reactivity of effector T cells is tightly regulated by at least two major subsets of CD4+ T cells: those that express the Foxp3+ gene (CD4+ CD25+ Foxp3+ T-reg cells) and those that do not express Foxp3− (CD4+ Foxp3− T cells). FOXp3+ T regs are divided into natural T-regs (n-T-regs) that are polarized during thymic education and induced FOXp3+ T regs (i-T-regs) that are primarily polarized by TGF-β. CD4+ Foxp3− T-regs fall into two major subtypes based on their cytokine profile: those that predominantly produce TGF-β (Th3) and those that mostly secrete IL-10 (Tr1).

Depletion of Foxp3+ CD4+ T cells has been described to result in the development of various inflammatory autoimmune diseases, such as systemic lupus erythematosus (SLE) [Alvarado-Sánchez B et al., J Autoimmun. (2006) 27 (2): 110-8] and X-linked IPEX syndrome (Immunodysregulation, Polyendocrinopathy, and Enteropathy, X-linked) [Bennett C L et al., Nat Genet. (2001) 27:20-21] while targeted expression of Foxp3 in Foxp3− cells has been described to induce regulatory T cells that suppress autoimmunity [Hori, S. et al. (2003) Science 299(5609): 1057-1061].

Various approaches for disease treatment via neutralization/antagonism of the C—C chemokine CCL1 (Chemokine ligand 1) have been described, some are summarized infra.

PCT Application No. WO 2003/051921 discloses mutants of CC-chemokines (e.g. CCL1) for the treatment of autoimmune and inflammatory diseases, cancer, or bacterial and viral infections. The CC-chemokine mutants described therein contain a single non-conservative substitution, in a consensus sequence common to a subset of CC-chemokines, and act as an antagonist of the CC-chemokine.

PCT Application No. WO 2003/035105 discloses synthetic chimeric fusion proteins for immuno-therapeutic uses (e.g. treatment of cancer or infectious diseases). The fusion proteins described are bi-functional and comprise two different elements (e.g. cytokines, chemokines, interferons or their respective receptors) linked by a linker peptide.

U.S. Patent Application No. 20090214533 discloses an agent for suppressing regulatory T cell function (or depleting/decreasing T regulatory cell number) in order to increase effector cell responses (e.g. anti-pathogen/tumor). The agents described therein comprise, for example, a fusion protein with a targeting moiety and a toxic moiety, wherein the targeting moiety targets and neutralizes CCL1 activity.

U.S. Patent Application No. 20020111290 discloses methods of diagnosing or evaluating skin injuries or conditions (e.g. lupus erythematosus, atopic dermatitis, inflammatory conditions) by evaluating expression of a chemokine (e.g. CCL1) or a chemokine receptor. U.S. Patent Application No. 20020111290 further discloses methods of treating these conditions by administering an antagonist of the chemokine or chemokine receptor.

Additional art include Mira E et al., J Immunol. (2008) 181:3524-3534, Broady R and Levings M K. Nat Med. (2008) 14: 1155-1156 and Cohen et al., JEM (2002) J Exp Med 196(3): 401-406.

SUMMARY OF THE INVENTION

According to an aspect of some embodiments of the present invention there is provided a method of treating a medical condition in which suppression of effector T cells is beneficial in a subject in need thereof, the method comprising administering to the subject a therapeutically effective amount of a CCL1 polypeptide, thereby treating the medical condition in the subject.

According to an aspect of some embodiments of the present invention there is provided a CCL1 polypeptide for use in the treatment of a medical condition in which suppression of effector T cells is beneficial.

According to an aspect of some embodiments of the present invention there is provided a method of suppressing effector T cells in a subject in need thereof, the method comprising administering to the subject a CCL1 polypeptide, thereby suppressing the effector T cells in the subject.

According to an aspect of some embodiments of the present invention there is provided a method of inducing production of CD4$^+$CD25$^+$FOXp3$^+$ T cells, the method comprising contacting a biological sample comprising CD4+ Foxp3− T cells with a CCL1 polypeptide, thereby inducing production of the CD4$^+$CD25$^+$FOXp3$^+$ T cells.

According to an aspect of some embodiments of the present invention there is provided a molecule comprising at least one CCL1 polypeptide attached to non-proteinaceous non-toxic moiety.

According to an aspect of some embodiments of the present invention there is provided a pharmaceutical composition comprising as an active ingredient the isolated polypeptide and a pharmaceutically acceptable carrier.

According to some embodiments of the invention, the biological sample is selected from the group consisting of a cell population, a blood, a bone marrow, a spinal fluid and a cord blood.

According to some embodiments of the invention, the cell population is obtained by blood apheresis.

According to some embodiments of the invention, the biological sample further comprises effector T cells.

According to some embodiments of the invention, the method is effected ex-vivo.

According to some embodiments of the invention, the method further comprises contacting the CD4+ Foxp3− T cells with an activating agent.

According to some embodiments of the invention, the activating agent is selected from the group consisting of an anti-CD3 antibody, an anti-CD28 antibody, a phorbol myristate acetate (PMA), a concanavalin A (ConA) and a MOGp35-55.

According to some embodiments of the invention, the CD4$^+$CD25$^+$FOXp3$^+$CD4+ T cells for treating a medical condition in which suppression of effector T cells is beneficial in a subject in need thereof.

According to some embodiments of the invention, the CD4$^+$CD25$^+$FOXp3$^+$CD4+ T cells for treating or preventing a transplantation related disease in a subject in need thereof.

According to some embodiments of the invention, the CD4+ Foxp3− T cells are derived from a donor non-syngeneic with respect to the subject.

According to some embodiments of the invention, the method further comprises contacting the CD4+ Foxp3− T cells in the presence of irradiated cells of the subject.

According to some embodiments of the invention, the CD4+ Foxp3− T cells are derived from the subject.

According to some embodiments of the invention, the method further comprising administering the CD4$^+$CD25$^+$FOXp3$^+$ T cells to the subject.

According to some embodiments of the invention, the method is effected in-vivo in a subject in need thereof.

According to some embodiments of the invention, the subject has a medical condition in which suppression of effector T cells is beneficial.

According to some embodiments of the invention, the medical condition is selected from the group consisting of an inflammatory disease, an autoimmune disease and a transplantation related disease.

According to some embodiments of the invention, the CCL1 is attached to a heterologous amino acid sequence.

According to some embodiments of the invention, the heterologous amino acid sequence comprises an immunoglobulin amino acid sequence.

According to some embodiments of the invention, the immunoglobulin amino acid sequence comprises a constant region of IgG1 Fc.

According to some embodiments of the invention, the CCL1 is as set forth in SEQ ID NO: 10.

According to some embodiments of the invention, the autoimmune disease is multiple sclerosis (MS).

According to some embodiments of the invention, the autoimmune disease is selected from the group consisting of systemic lupus erythematosis, multiple sclerosis, myasthenia gravis, progressive systemic sclerosis, hyperimmunoglobin E, Hashimoto's thyroiditis, familial Mediterranean fever, Grave's disease, autoimmune haemolytic anemia, primary biliary cirrhosis, diabetes mellitus type I and diabetes mellitus type II.

According to some embodiments of the invention, the inflammatory disease is selected from the group consisting of rheumatoid arthritis, rheumatoid spondylitis, osteroarthritis, gouty arthritis, arthritic conditions, inflamed joints, eczema, inflammatory skin conditions, inflammatory eye conditions, conjunctivitis, pyresis, tissue necrosis resulting from inflammation, atopic dermatitis, hepatitis B antigen negative chronic active hepatitis, Crohn's disease and ulcerative colitis, airway inflammation, asthma, bronchitis and inflammatory bowel disease.

According to some embodiments of the invention, the transplantation related disease is graft versus host disease (GVHD).

According to some embodiments of the invention, the transplantation related disease is graft rejection.

According to some embodiments of the invention, the amino acid sequence of the CCL1 is as set forth in SEQ ID NO: 8.

According to some embodiments of the invention, the non-proteinaceous non-toxic moiety is selected from the group consisting of polyethylene glycol (PEG), Polyvinyl pyrrolidone (PVP), poly(styrene comaleic anhydride) (SMA), and divinyl ether and maleic anhydride copolymer (DIVEMA).

According to some embodiments of the invention, the at least one CCL1 polypeptide comprises two polypeptides.

According to some embodiments of the invention, the isolated polypeptide being soluble under physiological conditions.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 2A-C are dot plot graphs depicting the effect of CCL1 on induction of FOXp3+ T-reg cell expansion. $10^6$ CD4+ T cells obtained from spleens of naïve mice were incubated with anti-CD3/CD28 antibody for 72 hrs in DMEM stimulation medium supplemented without CCL1 (FIG. 2A) or with different concentrations of mouse CCL1 (50 or 200 ng, FIGS. 2B-C, respectively) and analyzed for the expression of Foxp3 in CD4+ subsets.

FIGS. 3A-C are schematic illustrations depicting the generation of stable CCL1-IgG-expressing cell lines. Expression and purification of CCL1-Ig fusion proteins was carried out using CHO dhfr$^{-/-}$ (DG44) cells as previously described [Carothers A M et al., Biotechniques. (1989) 7:494-496, 498-499]. The CCL1-Ig fusion proteins were expressed as disulphide-linked homodimers, similar to IgG1, and were purified from the culture medium by a High-Trap protein G affinity column (BD Biosciences, Piscataway, N.J.).

FIG. 4A is a western blot analysis showing CCL1-Ig induced phosphorylation of ERK1/2 in bw5147 thymoma cells. $5 \times 10^6$ bw5147 cells were incubated in DMEM medium supplemented with 250 ng CCL1-Ig for different durations (as indicated) and were tested for ERK1/2 phosphorylation by western blot analysis. FIG. 4B is a graph showing CCL1-Ig induced Bw5147 cell migration. $10^6$ bw5147 thymoma cells were incubated in 100 μl DMEM medium in the upper chamber of a 6.5-mm diameter, 5-μm-pore polycarbonate Transwell culture-insert (Costar, Cambridge, Mass.) while the lower chamber contained different doses of CCL1-Ig. The number of cells that migrated towards the lower chamber were counted and divided by the spontaneous number of cells that were migrated in the chamber containing no chemokine.

FIG. 5A—on days 13, 15, 17, and 19 after the induction of disease, mice were injected i.p. either with PBS control (squares) or with 300 μg/mouse of mCCL1-Ig (circles). An observer blind to the experimental protocol monitored the development and progression of disease. The results (n=6 mice per each group) are shown as the mean maximal score±SE. FIG. 5B—on days 12, 14, 16, and 18 after the induction of disease, mice were injected i.p. either with PBS control (squares), with 300 μg/mouse of mCCL1-Ig (circles) or with IgG (triangles). An observer blind to the experimental protocol monitored the development and progression of disease. The results (n=6 mice per each group) are shown as the mean maximal score±SE. The arrow indicates the first day of mCCL1-Ig administration.

FIGS. 7A-F are dot plot graphs depicting the induced effect of CCL1 on CD4+ T regulatory cells in a bi-directional MLR assay. CD4+ T cells (C57b6—FOXP3 GFP) were incubated with non-CD4 Balb/c splenocytes for 7 days in the presence of CCL1 (FIGS. 7B-D: 10, 50 or 250 ng CCL1, respectively), CCL21 (FIG. 7F) or TGF-β (FIG. 7E) and measured for the ability to induce Foxp3+ T regulatory cells (Treg).

FIG. 9A presents a comparison between the colon length of control, healthy and CCl1-Ig treated mice after sacrifice on day seven;

FIG. 9B presents a comparison between the macroscopic assessment of the colon damage of control, healthy and CCl1-Ig treated mice after sacrifice on day seven.

DESCRIPTION OF SPECIFIC EMBODIMENTS OF THE INVENTION

The present invention, in some embodiments thereof, relates to CCL1 molecules and, more particularly, but not exclusively, to the use of same for therapy, such as of inflammatory, autoimmune and transplantation-related diseases.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The C—C chemokine CCL1 is secreted by activated T cells and mediates its biological activity by binding to the receptor CCR8. Interestingly, previous studies have suggested neutralization/antagonism of CCL1 for the treatment of autoimmune diseases, inflammatory diseases, cancer, bacterial infections and viral infections.

While reducing the present invention to practice, the present inventors have surprisingly uncovered that CCL1 is involved in induction of CD4+ CD25+ Foxp3+ T-regulatory cells and in suppression of effector T cells. This finding supports a new role for CCL1 in the treatment of autoimmune disorders and graft versus host disease (GVHD) as well as other medical conditions in which suppression of effector T cells is beneficial.

Figure 5A:
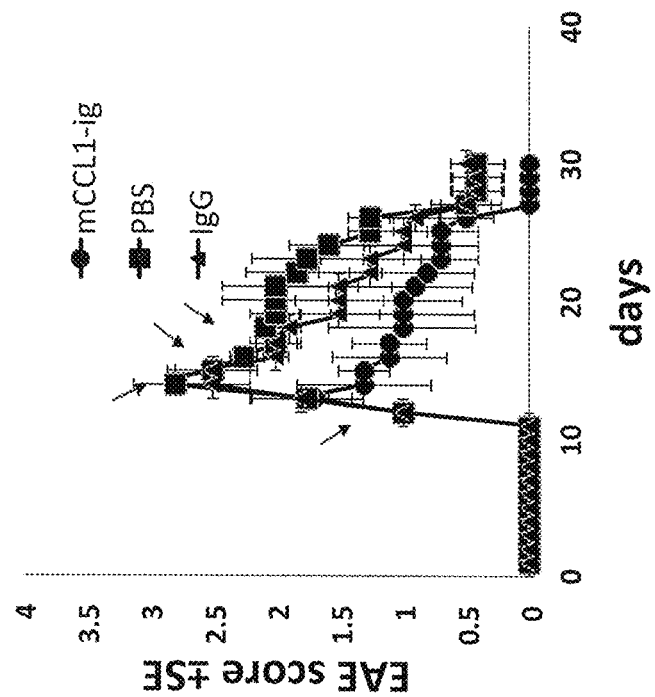
FIGS. 5A-B are line graphs illustrating the suppressor effect of CCL1-Ig on ongoing EAE. Two experiments were conducted showing that administration of mCCL1-Ig during ongoing EAE attenuated disease severity. C57BL/6 female mice (n=6 per group) which were subjected to active induction of MOGp35-55-induced EAE, and at the onset of disease (day 12—depicted by arrows) the mice were separated into two equally sick groups (n=6 mice per group).
Figure 5B:
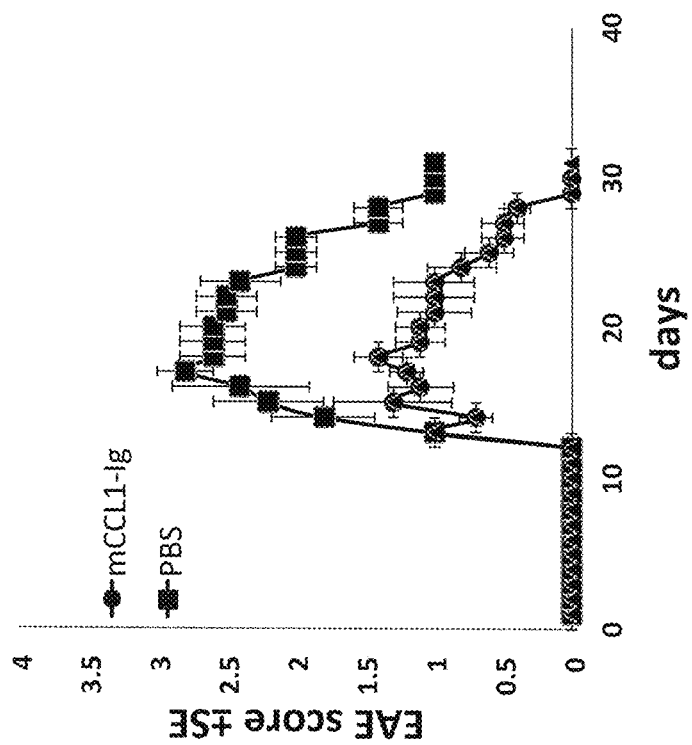
Figure 6:
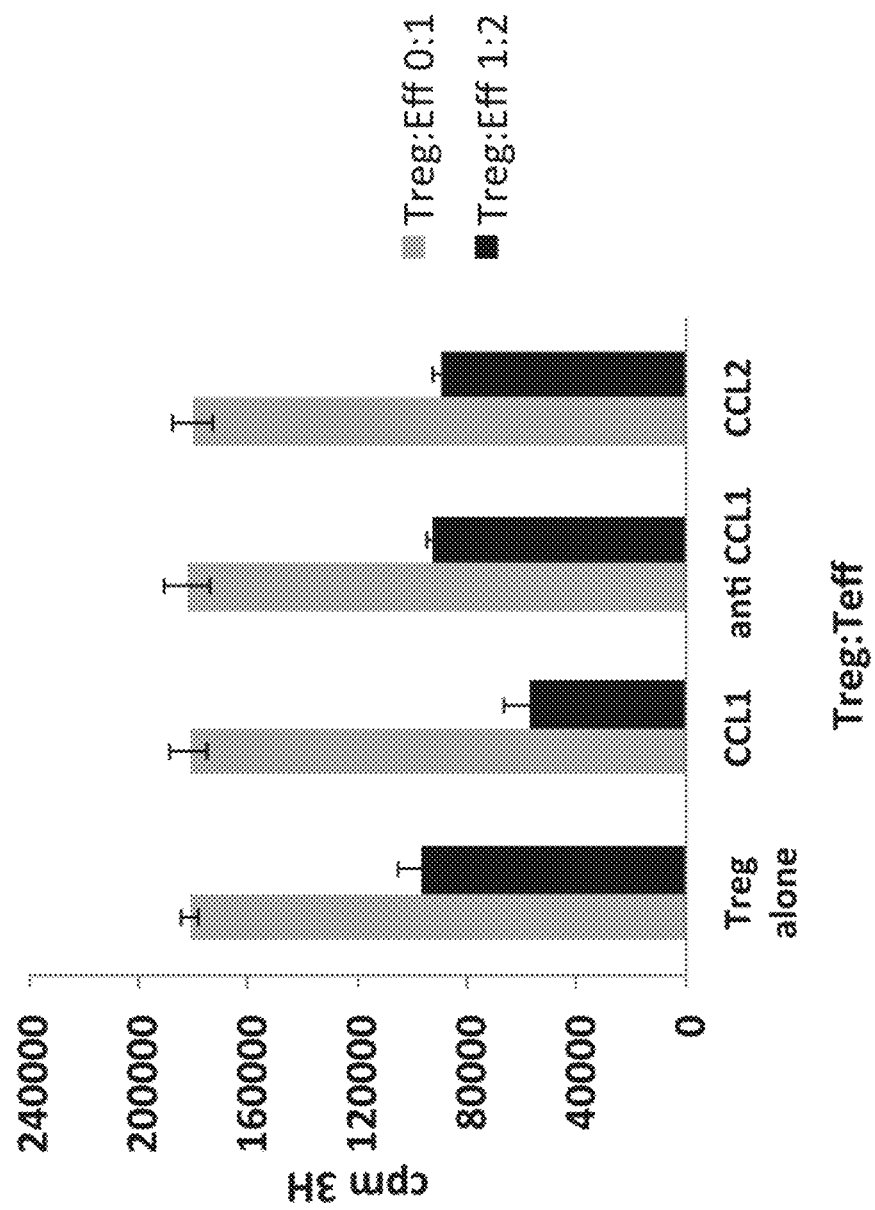
FIG. 6 is a graph depicting the enhanced effect of CCL1 on the suppressive activity of FOXP3 T regulatory cells in-vitro. CD4+CD25+FOXP3− T cells (T eff) were incubated with or without CD4+CD25+FOXP3+ T cells (T reg) in the presence of CCL1, anti-CCL1, CCL2 or medium alone. Cells were activated with anti-CD3/CD28 antibody and APC for 3 days. Proliferation was measured by thymidine (3H) uptake during the last 16 hours of incubation and radiation levels were represented as cpm (counts per minute).

Specifically, the present inventors have shown for the first time that CCL1 is directly involved in the induction of CD4+ Foxp3− T cells into CD4+ Foxp3+ T regulatory cells (FIGS. 1A-F and 2A-C) and in the suppression of Foxp3 effector cells (FIG. 6). The present inventors have generated CCL1-Ig fusion proteins (FIGS. 3A-C) which exhibited biological activity similar to that of native CCL1 (FIGS. 4A-C) and which efficiently suppressed ongoing EAE in mice (i.e. the murine experimental model for Multiple Sclerosis and other inflammatory autoimmune diseases, FIGS. 5A-B). Moreover, the CCL1-Ig fusion proteins generated by the present inventors significantly induced production of CD4+ Foxp3+ T regulatory cells in a GVHD in-vitro model (FIGS. 7A-F). Taken together the present teachings portray a therapeutic value of CCL1 molecules in treatment of autoimmune and transplantation related diseases.

Thus, according to one aspect of the present invention, there is provided a method of treating a medical condition in which suppression of effector T cells is beneficial in a subject in need thereof, the method comprising administering to the subject a therapeutically effective amount of a CCL1 polypeptide, thereby treating the medical condition in the subject.

As used herein the term "treating" refers to preventing, curing, reversing, attenuating, alleviating, minimizing, suppressing or halting the deleterious effects of a medical condition in which suppression of effector T cells is beneficial.

As used herein the phrase "medical condition in which suppression of effector T cells is beneficial" refers to any disease or disorder in which limiting or reducing the activity of effector T cells can prevent an occurrence of a disease or medical symptoms associated therewith or halt disease progression or medical symptoms associated therewith.

As used herein the term "effector T cells" refers to the subset of T cells, also known as memory T cells, which are a specialized subpopulation of antigen-specific T cells that persist for a long-term after an infection has resolved. Effector T cells may express the membrane markers CD4+ or CD8+.

As used herein the phrases "suppression of effector T cells" or "suppressing effector T cells" refers to reducing the activity or level of effector T cells by at least about 10%, 20%, 30%, 40%, 50%, 60%, 70%, 80%, 90% or at least by 100% as compared to untreated effector T cells.

Measuring the activity or level or effector T cells can be carried out using any method known to one of ordinary skill in the art, as for example, by measuring increased cell apoptosis (e.g. via cell staining of Anexin 5 expression on effector cells and flow cytometric analysis), by measuring decreased cell proliferation (e.g. via thymidine (3H) uptake), and by measuring reduced cytokine secretion such as INF-γ, TNF-α, IL-2 and IL-17 (e.g. via ELISA) by the effector T cells.

In addition, T regulatory cell (Treg) suppression assay can be used to measure the suppression of effector T cells in-vitro. Thus, for example, effector T cells can be incubated with T regulatory cells in the presence of CCL1 (about 100-500 ng), stimulatory agents, e.g. anti-CD3 antibody and/or anti-CD28 antibody (about 0.5-2 μg/ml) and APCs for several days (e.g. 2-5 days). Proliferation can then be measured by thymidine (3H) uptake during the last 16 hours of incubation [see, for example, Thornton and Shevach (1998). "CD4+CD25+ immunoregulatory T cells suppress polyclonal T cell activation in vitro by inhibiting interleukin 2 production." Journal of Experimental Medicine 188(2): 287-296].

The medical condition may comprise, for example, an inflammatory disease, an autoimmune disease or a transplantation related disease. It will be appreciated that the present teachings do not contemplate treating conditions in which suppression of effector T cells can be harmful, such as cancer. It is well known in the art that in cancer treatment, the activity of effector T cells should be elevated in order to improve disease treatment.

According to an embodiment of the present invention, the medical condition is an inflammatory autoimmune disease.

Herein, the phrase "autoimmune disease" refers to a disease resulting from a disordered immune reaction (e.g., antibody production) generated against components of one's own body (i.e. auto-antigens). According to the present teachings the autoimmune disease is associated at least in part with uncontrolled (increased) effector T cell activity. The immune system of the subject then activates an inflammatory cascade aimed at cells and tissues presenting those specific self antigens. The destruction of the antigen, tissue, cell type, or organ attacked by the individual's own immune system gives rise to the symptoms of the disease.

According to an embodiment of the present invention, the autoimmune disease is Multiple Sclerosis (MS), the inflammatory, demyelinating disease of the central nervous system (CNS) which is typically characterized by various symptoms of neurological dysfunction. Any type of Multiple Sclerosis may be treated according to the teachings of the present invention including relapsing-remitting, secondary progressive, primary progressive, progressive relapsing and special cases of MS with non-standard behavior (also referred to as borderline forms of MS), such as for example without limitation, Neuromyelitis optica (NMO), Balo concentric sclerosis, Schilder disease, Marburg multiple sclerosis, acute disseminated encephalomyelitis (ADEM) and autoimmune variants of peripheral neuropathies. The disease may be treated at any stage.

According to an embodiment of the present invention, the disease is systemic lupus erythematosis (SLE) or lupus nephritis.

According to an embodiment of the present invention, the disease is diabetes mellitus type I or diabetes mellitus type II.

According to an embodiment of the present invention, the disease is psoriasis.

According to another embodiment, the autoimmune disease is systemic lupus erythematosis (SLE), myasthenia gravis, progressive systemic sclerosis, hyperimmunoglobin E, Hashimoto's thyroiditis, familial Mediterranean fever, Grave's disease, autoimmune haemolytic anemia, primary biliary cirrhosis, diabetes mellitus type I and diabetes mellitus type II.

Additional autoimmune diseases which may be treated according to the present methods include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151

(3):178), antiphospholipid syndrome (Flamholz R et al., J Clin Apheresis 1999; 14 (4); 171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

It will be appreciated that the CCL1 of the present invention may also be used to treat inflammatory diseases.

The phrase "inflammatory disease", as used herein, refers to any disease or disorder which includes a component of inflammation, which is imperative to disease onset or progression. The inflammatory disease may be a chronic inflammatory disease, an acute inflammatory disease or a relapsing remitting disease.

According to an embodiment of the present invention, the inflammatory disease is rheumatoid arthritis, rheumatoid spondylitis, osteroarthritis, gouty arthritis, arthritic conditions, inflamed joints, eczema, inflammatory skin conditions, inflammatory eye conditions, conjunctivitis, pyresis, tissue necrosis resulting from inflammation, atopic dermatitis, hepatitis B antigen negative chronic active hepatitis, Crohn's disease and ulcerative colitis, airway inflammation, asthma, bronchitis or inflammatory bowel disease (IBD).

According to an embodiment of the present invention, the disease is inflammatory bowel disease (IBD).

According to an embodiment of the present invention, the disease is colitis.

According to an embodiment of the present invention, the disease is Crohn's disease.

According to an embodiment of the present invention, the disease is rheumatoid arthritis (RA).

According to another embodiment, the inflammatory disease is associated with hypersensitivity.

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol. Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 11 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al. Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12): 2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1

(2):140), connective tissue diseases, ear diseases, autoimmune connective tissue diseases, autoimmune ear disease (Yoo T J. et al., Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

The CCL1 of the present invention may also be used to treat transplantation related disease.

Herein, the phrase "transplantation related disease", refers to any disease or disorder which occurs following or as a result of a transplantation procedure or preconditioning thereto. The transplantation related disease may be a chronic disease or an acute disease and may occur at any stage or time following transplantation of a graft (e.g. several hours, several days, several weeks, several months or several years following transplantation).

It will be appreciated that the present teachings contemplate treatment of a transplantation related disease following transplantation of any graft including, for example, a solid organ or tissue graft (e.g. kidney, heart, lung, spleen, liver, skin, intestines, etc.) or a cell graft such as immature hematopoietic cells, including stem cells, which can be derived, for example, from bone marrow, mobilized peripheral blood (by for example leukapheresis), fetal liver, yolk sac and/or cord blood of the donor (e.g. non-syngeneic donor).

Examples of diseases associated with transplantation of a graft include, but are not limited to, graft rejection, chronic graft rejection, subacute graft rejection, hyperacute graft rejection, acute graft rejection and graft versus host disease (GVHD).

According to a specific embodiment, the transplantation related disease is graft versus host disease (GVHD).

According to another embodiment, the transplantation related disease is graft rejection.

As used herein, the term "subject" or "subject in need thereof" refers to a mammal, preferably a human being, male or female at any age that is in need of suppression of effector T cell activity (e.g. CD4+ or CD8+ effector T cells). Typically, the subject has been diagnosed with an autoimmune disease, an inflammatory disease or a transplantation related disease, however, the subject may also have been diagnosed with any other disease which is amenable to treatment via suppression of effector T cells. The subject may or may not have received previous treatment for the disease. Examples of such disorders are provided hereinabove.

According to the present teachings, a CCL1 polypeptide is used for the treatment of the medical condition in which suppression of effector T cells is beneficial.

As used herein the term "CCL1" refers to at least an active portion of a mammalian (e.g., human) C—C chemokine polypeptide having at least one functional property specific to CCL1. Accordingly, the CCL1 of the present invention may comprise the ability to attract monocytes, NK cells, and immature B cells and dendritic cells, and may bind to the cell surface chemokine receptor CCR8. Typically, CCL1 can induce production of CD4+ Foxp3+ T regulatory cells and can suppress T effector cells. According to a specific embodiment, the CCL1 of the present invention comprises at least one or all the above functional properties. An exemplary CCL1 amino acid sequence is as set forth in GenBank Accession No: NP_002972.1 (SEQ ID NO: 8). Any CCL1 known in the art can be used in accordance with the teachings of the present invention. For example, recombinant human CCL1 is available from Sigma-Aldrich, R&D Systems, Millipore and from GenScript. It will be appreciated that any active fragment of CCL1 may be used in accordance with the present teachings such as the N-terminal domain of CCL1, such a fragment is capable of binding CCR8.

The term "polypeptide" as used herein encompasses native peptides (either degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications, including but not limited to $CH_2$—NH, $CH_2$—S, $CH_2$—S=O, O=C—NH, $CH_2$—O, $CH_2$—$CH_2$, S=C—NH, CH=CH, and CF=CH; backbone modifications; and residue modifications. Methods for preparing peptidomimetic compounds are well known in the art and are specified, for example, in Ramsden, C. A., ed. (1992), Quantitative Drug Design, Chapter 17.2, F. Choplin Pergamon Press, which is incorporated by reference as if fully set forth herein. Further details in this respect are provided hereinbelow.

Peptide bonds (—CO—NH—) within the peptide may be substituted, for example, by N-methylated bonds (—N(CH3)-CO—); ester bonds (—C(R)H—C—O—O—C(R)—N—); ketomethylene bonds (—CO—CH2-); α-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH—); olefinic double bonds (—CH=CH—); retro amide bonds (—NH—CO—); and peptide derivatives (—N(R)—CH2-CO—), wherein R is the "normal" side chain, naturally presented on the carbon atom. These modifications can occur at any of the bonds along the peptide chain and even at several (2-3) at the same time.

Natural aromatic amino acids, Trp, Tyr, and Phe, may be substituted for synthetic non-natural acids such as, for instance, tetrahydroisoquinoline-3-carboxylic acid (TIC), naphthylelanine (Nol), ring-methylated derivatives of Phe, halogenated derivatives of Phe, and o-methyl-Tyr, as long as the functionality as retained.

In addition to the above, the polypeptides of the present invention may also include one or more modified amino acids or one or more non-amino acid monomers (e.g., fatty acids, complex carbohydrates, etc.).

The term "amino acid" or "amino acids" is understood to include the 20 naturally occurring amino acids; those amino acids often modified post-translationally in vivo, including, for example, hydroxyproline, phosphoserine, and phosphothreonine; and other less common amino acids, including but not limited to 2-aminoadipic acid, hydroxylysine, isodesmosine, nor-valine, nor-leucine, and ornithine. Furthermore, the term "amino acid" includes both D- and L-amino acids.

The peptides of the present invention are preferably utilized in a linear form, although it will be appreciated that in cases where cyclicization does not severely interfere with peptide characteristics, cyclic forms of the peptide can also be utilized.

The peptides of the present invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of the present invention involves solid phase peptide synthesis.

Large scale peptide synthesis is described by Andersson Biopolymers 2000; 55 (3):227-50.

According to an embodiment of the present invention, CCL1 is attached to a heterologous amino acid sequence.

As used herein the phrase "heterologous amino acid sequence" refers to an amino acid sequence which does not endogenously form a part of the CCL1 amino acid sequence. Preferably, the heterologous amino acid sequence does not down-regulate the biological activity of the CCL1 polypeptide (e.g. induction of CD4+ Foxp3+ T regulatory cells).

The heterologous amino acid sequence may thus serve to ensure stability of the CCL1 of the present invention without compromising its activity. For example, the heterologous polypeptide may increase the half-life of the CCL1 chimeric molecule in the serum.

Examples of heterologous amino acid sequences that may be used in accordance with the teachings of the present invention include, but are not limited to, immunoglobulin, galactosidase, glucuronidase, glutathione-S-transferase (GST), carboxy terminal peptide (CTP) from chorionic gonadotrophin (CGβ) and chloramphenicol acetyltransferase (CAT) [see for example Suzuki et al., supra; and U.S. Publication No. 20030171551]. According to a specific embodiment, the heterologous amino acid sequence is an immunoglobulin.

Generally the heterologous amino acid sequence is localized at the amino- or carboxyl-terminus (n-ter or c-ter, respectively) of the CCL1 polypeptide of the present invention. The heterologous amino acid sequence may be attached to the CCL1 amino acid sequence by any of peptide or non-peptide bond. Attachment of the CCL1 amino acid sequence to the heterologous amino acid sequence may be effected by direct covalent bonding (peptide bond or a substituted peptide bond) or indirect binding such as by the use of a linker having functional groups. Functional groups include, without limitation, a free carboxylic acid (C(=O) OH), a free amino group (NH$_2$), an ester group (C(=O)OR, where R is alkyl, cycloalkyl or aryl), an acyl halide group (C(=O)A, where A is fluoride, chloride, bromide or iodide), a halide (fluoride, chloride, bromide or iodide), a hydroxyl group (OH), a thiol group (SH), a nitrile group (C≡N), a free C-carbamic group (NR"—C(=O)—OR', where each of R' and R" is independently hydrogen, alkyl, cycloalkyl or aryl).

An example of a heterologous amino acid sequence which may be used in accordance with this aspect of the present invention is an immunoglobulin amino acid sequence, such as the hinge and Fc regions of an immunoglobulin heavy domain (see U.S. Pat. No. 6,777,196). The immunoglobulin moiety in the chimeras of this aspect of the present invention may be obtained from IgG1, IgG2, IgG3 or IgG4 subtypes, IgA, IgE, IgD or IgM, as further discussed hereinbelow. An exemplary human CCL1 polypeptide linked to an IgG1 moiety is set forth in SEQ ID NO: 10.

Typically, in such fusions the chimeric molecule will retain at least functionally active hinge and CH2 and CH3 domains of the constant region of an immunoglobulin heavy chain. Fusions can also be generated to the C-terminus of the Fc portion of a constant domain, or immediately N-terminal to the CH1 of the heavy chain or the corresponding region of the light chain.

Though it may be possible to conjugate the entire heavy chain constant region to the CCL1 amino acid sequence of the present invention, it is preferable to fuse shorter sequences. For example, a sequence beginning at the hinge region upstream of the papain cleavage site, which defines IgG Fc chemically; residue 216, taking the first residue of heavy chain constant region to be 114, or analogous sites of other immunoglobulins, may be used in the fusion. In a particular embodiment, the CCL1 amino acid sequence is fused to the hinge region and CH2 and CH3, or to the CH1, hinge, CH2 and CH3 domains of an IgG2, or IgG3 heavy chain (see U.S. Pat. No. 6,777,196).

As mentioned, the immunoglobulin sequences used in the construction of the chimeric molecules of this aspect of the present invention may be from an IgG immunoglobulin heavy chain constant domain. According to one embodiment of the present invention, the IgG immunoglobulin sequence is for example as set forth in SEQ ID NO: 6. Such IgG immunoglobulin sequence can be purified efficiently on, for example, immobilized protein A. Selection of a fusion partner may also take into account structural and functional properties of immunoglobulins. Thus, for example, the heterologous peptide may be IgG3 hinge which is longer and more flexible, so it can accommodate larger CCL1 amino acid sequences that may not fold or function properly when fused to IgG1. Another consideration may be valency; IgG are bivalent homodimers, whereas Ig subtypes like IgA and IgM may give rise to dimeric or pentameric structures, respectively, of the basic Ig homodimer unit. Other considerations in selecting the immunoglobulin portion of the chimeric molecules of this aspect of the present invention are described in U.S. Pat. No. 6,77,196.

The CCL1 fusion polypeptides of the present invention can be generated using recombinant techniques such as described by Bitter et al. (1987) Methods in Enzymol. 153:516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988, Methods for Plant Molecular Biology, Academic Press, NY, Section VIII, pp 421-463.

The heterologous peptides may also be chemically linked to CCL1 following the independent generation of each. Thus, the two peptides may be covalently or non-covalently linked using any linking or binding method and/or any suitable chemical linker known in the art. Such linkage can be direct or indirect, as by means of a peptide bond or via covalent bonding to an intervening linker element, such as a linker peptide or other chemical moiety, such as an organic polymer. Such chimeric peptides may be linked via bonding at the carboxy (C) or amino (N) termini of the peptides, or via bonding to internal chemical groups such as straight, branched, or cyclic side chains, internal carbon or nitrogen atoms, and the like. The exact type and chemical nature of such cross-linkers and cross linking methods is preferably adapted to the type and nature of the peptides used.

According to one embodiment of this aspect of the present invention, the CCL1 fusion protein of this aspect of the present invention is encoded by a nucleic acid sequences as set forth in SEQ ID NO: 9.

Thus, molecules of this aspect of the present invention may comprise heterologous amino acid sequences, as described above. Additionally or alternatively, CCL1 amino acid sequences of the present invention may be attached to a non-proteinaceous non-toxic moiety. According to one embodiment, the CCL1 molecules are also selected non-immunogenic in a subject.

The phrase "non-proteinaceous non-toxic moiety" as used herein refers to a molecule not including peptide bonded amino acids that is attached to the above-described CCL1 amino acid sequence. Exemplary non-proteinaceous non-toxic moieties which may be used according to the present teachings include, but are not limited to, polyethylene glycol (PEG), Polyvinyl pyrrolidone (PVP), poly(styrene comaleic anhydride) (SMA), and divinyl ether and maleic anhydride copolymer (DIVEMA).

Such a molecule is highly stable (resistant to in-vivo proteolytic activity probably due to steric hindrance conferred by the non-proteinaceous moiety) and may be produced using common solid phase synthesis methods which are inexpensive and highly efficient, as further described hereinbelow. However, it will be appreciated that recombinant techniques may still be used, whereby the recombinant peptide product is subjected to in-vitro modification (e.g., PEGylation as further described hereinbelow).

It will be appreciated that such non-proteinaceous non-toxic moieties may also be attached to the above mentioned fusion molecules (i.e., which comprise a heterologous amino acid sequence) to promote stability and possibly solubility of the molecules.

Bioconjugation of such a non-proteinaceous non-toxic moiety (such as PEGylation) can confer the CCL1 amino acid sequence with stability (e.g., against protease activities) and/or solubility (e.g., within a biological fluid such as blood, digestive fluid) while preserving its biological activity and prolonging its half-life.

Bioconjugation is advantageous particularly in cases of therapeutic proteins which exhibit short half-life and rapid clearance from the blood. The increased half-lives of bioconjugated proteins in the plasma results from increased size of protein conjugates (which limits their glomerular filtration) and decreased proteolysis due to polymer steric hindrance. Generally, the more polymer chains attached per peptide, the greater the extension of half-life. However, measures are taken not to reduce the specific activity of the CCL1 amino acid sequence of the present invention (i.e., induction of CD4+ Foxp3+ T regulatory cells).

Bioconjugation of the CCL1 amino acid sequence with PEG (i.e., PEGylation) can be effected using PEG derivatives such as N-hydroxysuccinimide (NHS) esters of PEG carboxylic acids, monomethoxy$PEG_2$-NHS, succinimidyl ester of carboxymethylated PEG (SCM-PEG), benzotriazole carbonate derivatives of PEG, glycidyl ethers of PEG, PEG p-nitrophenyl carbonates (PEG-NPC, such as methoxy PEG-NPC), PEG aldehydes, PEG-orthopyridyl-disulfide, carbonyldimidazol-activated PEGs, PEG-thiol, PEG-maleimide. Such PEG derivatives are commercially available at various molecular weights [See, e.g., Catalog, Polyethylene Glycol and Derivatives, 2000 (Shearwater Polymers, Inc., Huntsville, Ala.)]. If desired, many of the above derivatives are available in a monofunctional monomethoxyPEG (mPEG) form. In general, the PEG added to the CCL1 amino acid sequence of the present invention should range from a molecular weight (MW) of several hundred Daltons to about 100 kDa (e.g., between 3-30 kDa). Larger MW PEG may be used, but may result in some loss of yield of PEGylated peptides. The purity of larger PEG molecules should be also watched, as it may be difficult to obtain larger MW PEG of purity as high as that obtainable for lower MW PEG. It is preferable to use PEG of at least 85% purity, and more preferably of at least 90% purity, 95% purity, or higher. PEGylation of molecules is further discussed in, e.g., Hermanson, Bioconjugate Techniques, Academic Press San Diego, Calif. (1996), at Chapter 15 and in Zalipsky et al., "Succinimidyl Carbonates of Polyethylene Glycol," in Dunn and Ottenbrite, eds., Polymeric Drugs and Drug Delivery Systems, American Chemical Society, Washington, D.C. (1991).

Conveniently, PEG can be attached to a chosen position in the CCL1 amino acid sequence by site-specific mutagenesis as long as the activity of the conjugate is retained (e.g. induction of CD4+ Foxp3+ T regulatory cells). A target for PEGylation could be any Cysteine residue at the N-terminus or the C-terminus of the CCL1 amino acid sequence. Additionally or alternatively, other Cysteine residues can be added to the CCL1 amino acid sequence (e.g., at the N-terminus or the C-terminus) to thereby serve as a target for PEGylation. Computational analysis may be effected to select a preferred position for mutagenesis without compromising the activity.

Various conjugation chemistries of activated PEG such as PEG-maleimide, PEG-vinylsulfone (VS), PEG-acrylate (AC), PEG-orthopyridyl disulfide can be employed. Methods of preparing activated PEG molecules are known in the arts. For example, PEG-VS can be prepared under argon by reacting a dichloromethane (DCM) solution of the PEG-OH with NaH and then with di-vinylsulfone (molar ratios: OH 1:NaH 5:divinyl sulfone 50, at 0.2 gram PEG/mL DCM). PEG-AC is made under argon by reacting a DCM solution of the PEG-OH with acryloyl chloride and triethylamine (molar ratios: OH 1:acryloyl chloride 1.5:triethylamine 2, at 0.2 gram PEG/mL DCM). Such chemical groups can be attached to linearized, 2-arm, 4-arm, or 8-arm PEG molecules.

While conjugation to cysteine residues is one convenient method by which the CCL1 amino acid of the present invention can be PEGylated, other residues can also be used if desired. For example, acetic anhydride can be used to react with $NH_2$ and SH groups, but not COOH, S—S, or —$SCH_3$ groups, while hydrogen peroxide can be used to react with —SH and —$SCH_3$ groups, but not $NH_2$. Reactions can be conducted under conditions appropriate for conjugation to a desired residue in the peptide employing chemistries exploiting well-established reactivities.

For bioconjugation of the CCL1 amino acid sequence of the present invention with PVP, the terminal COOH-bearing PVP is synthesized from N-vinyl-2-pyrrolidone by radical polymerization in dimethyl formamide with the aid of 4,4'-azobis-(4-cyanovaleric acid) as a radical initiator, and 3-mercaptopropionic acid as a chain transfer agent. Resultant PVPs with an average molecular weight of Mr 6,000 can be separated and purified by high-performance liquid chromatography and the terminal COOH group of synthetic PVP is activated by the N-hydroxysuccinimide/dicyclohexyl carbodiimide method. The CCL1 amino acid sequence is reacted with a 60-fold molar excess of activated PVP and the reaction is stopped with amino caploic acid (5-fold molar excess against activated PVP), essentially as described in Haruhiko Kamada, et al., 2000, Cancer Research 60: 6416-6420, which is fully incorporated herein by reference.

Resultant conjugated CCL1 molecules (e.g., PEGylated or PVP-conjugated CCL1) are separated, purified and qualified using e.g., high-performance liquid chromatography (HPLC). In addition, purified conjugated molecules of this aspect of the present invention may be further qualified using e.g., in vitro assays in which the binding specificity of CCL1 ligand to its receptor (e.g., CCR8) is tested in the presence or absence of the CCL1 conjugates of the present invention, essentially as described for other chemokines [e.g., MIP-1$\alpha$, see for example, Hesselgesser J (1998)].

Molecules of this aspect of present invention can be biochemically synthesized such as by using standard solid phase techniques. These methods include exclusive solid phase synthesis, partial solid phase synthesis methods, fragment condensation and classical solution synthesis. These methods are preferably used when the peptide is relatively short (i.e., 10 kDa) and/or when it cannot be produced by recombinant techniques (i.e., not encoded by a nucleic acid sequence) and therefore involve different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the peptides of the present invention can be generated using recombinant techniques such as described by Bitter et al. (1987) Methods in Enzymol. 153:516-544; Studier et al. (1990) Methods in Enzymol. 185:60-89; Brisson et al. (1984) Nature 310:511-514; Takamatsu et al. (1987) EMBO J. 6:307-311; Coruzzi et al. (1984) EMBO J. 3:1671-1680; Brogli et al. (1984) Science 224:838-843; Gurley et al. (1986) Mol. Cell. Biol. 6:559-565 and Weissbach & Weissbach, 1988, Methods for Plant Molecular Biology, Academic Press, NY, Section VIII, pp 421-463.

Briefly, an expression construct (i.e., expression vector), which includes an isolated polynucleotide (i.e., isolated from a naturally occurring source thereof, e.g., SEQ ID NO: 7) which comprises a nucleic acid sequence encoding the CCL1 amino acid sequence (optionally in frame fused to a nucleic acid sequence encoding the heterologous amino acid sequence e.g., SEQ ID NO: 5) of the present invention positioned under the transcriptional control of a regulatory element, such as a promoter, is introduced into host cells.

For example, a nucleic acid sequence encoding a CCL1 peptide of the present invention (e.g., SEQ ID NO: 7) is ligated in frame to an immunoglobulin cDNA sequence (e.g., SEQ ID NO: 5). It will be appreciated that, ligation of genomic immunoglobulin fragments can also be used. In this case, fusion requires the presence of immunoglobulin regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. The nucleic acid sequences encoding the CCL1 amino acid sequence and immunoglobulin can be ligated in tandem into an expression construct (vector) that directs efficient expression in the selected host cells, further described hereinbelow. For expression in mammalian cells, pRK5-based vectors [Schall et al., Cell, 61:361-370 (1990)]; and CDM8-based vectors [Seed, Nature, 329:840 (1989)] can be used. The exact junction can be created by removing the extra sequences between the designed junction codons using oligonucleotide-directed deletional mutagenesis [Zoller et al, Nucleic Acids Res., 10:6487 (1982); Capon et al., Nature, 337:525-531 (1989)]. Synthetic oligonucleotides can be used, in which each half is complementary to the sequence on either side of the desired junction; ideally, these are 11 to 48-mers. Alternatively, PCR techniques can be used to join the two parts of the molecule in-frame with an appropriate vector.

Methods of introducing the expression construct into a host cell are well known in the art and include, electroporation, lipofection and chemical transformation (e.g., calcium phosphate). See also Example 2 of the Examples section which follows.

The "transformed" cells are cultured under suitable conditions, which allow the expression of the chimeric molecule encoded by the nucleic acid sequence.

Following a predetermined time period, the expressed chimeric molecule is recovered from the cell or cell culture, and purification is effected according to the end use of the recombinant polypeptide.

Depending on the host/vector system utilized, any of a number of suitable transcription and translation elements including constitutive and inducible promoters, transcription enhancer elements, transcription terminators, and the like, can be used in the expression vector [see, e.g., Bitter et al., (1987) Methods in Enzymol. 153:516-544].

Other than containing the necessary elements for the transcription and translation of the inserted coding sequence (encoding the chimera), the expression construct of the present invention can also include sequences engineered to optimize stability, production, purification, yield or toxicity of the expressed fusion protein.

A variety of prokaryotic or eukaryotic cells can be used as host-expression systems to express the fusion protein coding sequence. These include, but are not limited to, microorganisms, such as bacteria transformed with a recombinant bacteriophage DNA, plasmid DNA or cosmid DNA expression vector containing the chimera coding sequence; yeast transformed with recombinant yeast expression vectors containing the chimera coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the chimera coding sequence. Mammalian expression systems are preferably used to express the chimera of the present invention.

The choice of host cell line for the expression of the molecules depends mainly on the expression vector. Eukaryotic expression systems are preferred (e.g., mammalian and insects) since they allow post translational modifications (e.g., glycosylation). Another consideration is the amount of protein that is required. Milligram quantities often can be produced by transient transfections. For example, the adenovirus EIA-transformed 293 human embryonic kidney cell line can be transfected transiently with pRK5-based vectors by a modification of the calcium phosphate method to allow efficient expression. CDM8-based vectors can be used to transfect COS cells by the DEAE-dextran method (Aruffo et al., Cell, 61:1303-1313 (1990); Zettmeissl et al., DNA Cell Biol. US, 9:347-353 (1990)]. If larger amounts of protein are desired, the molecules can be expressed after stable transfection of a host cell line (see Example 1 of the Examples section). It will be appreciated that the presence of a hydrophobic leader sequence at the N-terminus of the molecule will ensure processing and secretion of the molecule by the transfected cells.

It will be appreciated that the use of bacterial or yeast host systems may be preferable to reduce cost of production. However since bacterial host systems are devoid of protein glycosylation mechanisms, a post production glycosylation may be needed.

In any case, transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant chimera molecule of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell, secreted into the fermentation medium, secreted into a space between two cellular membranes, such as the periplasmic space in E. coli; or retained on the outer surface of a cell or viral membrane.

Following a predetermined time in culture, recovery of the recombinant protein is effected. The phrase "recovering the recombinant protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Molecules of the present invention are preferably retrieved in "substantially pure" form. As used herein, "substantially pure" refers to a purity that allows for the effective use of the protein in the applications, described herein.

Recombinant molecules of the present invention can be conveniently purified by affinity chromatography. The suitability of protein A as an affinity ligand depends on the species and isotype of the immunoglobulin Fc domain that is used in the chimera. Protein A can be used to purify chimeric molecules that are based on human γ1, γ2, or γ4 heavy chains [Lindmark et al., J. Immunol. Meth., 62:1-13 (1983)]. Protein G is preferably used for mouse isotypes and for human γ3 [Guss et al., EMBO J., 5:1567-1575 (1986)]. The solid support to which the affinity ligand is attached is most often agarose, but other solid supports are also available. Mechanically stable solid supports such as controlled pore glass or poly(styrenedivinyl)benzene allow for faster flow rates and shorter processing times than can be achieved with agarose. The conditions for binding the chimeric molecules to the protein A or G affinity column are dictated entirely by the characteristics of the Fc domain; that is, its species and isotype. Generally, when the proper ligand is chosen, efficient binding occurs directly from unconditioned culture fluid. One distinguishing feature of chimeric molecules of this aspect of the present invention is that, for human .gamma.1 molecules, the binding capacity for protein A is somewhat diminished relative to an antibody of the same Fc type. Bound chimeric molecules of this aspect of the present invention can be efficiently eluted either at acidic pH (at or above 3.0), or in a neutral pH buffer containing a mildly chaotropic salt. This affinity chromatography step can result in a chimeric molecule preparation that is >95% pure. Medical grade purity is essential for therapeutic applications.

Other methods known in the art can be used in place of, or in addition to, affinity chromatography on protein A or G to purify chimeric molecules which include an immunoglobulin portion. Such chimeric molecules behave similarly to antibodies in thiophilic gel chromatography [Hutchens et al., Anal. Biochem., 159:217-226 (1986)] and immobilized metal chelate chromatography [Al-Mashikhi et al., J. Dairy Sci., 71:1756-1763 (1988)]. In contrast to antibodies, however, their behavior on ion exchange columns is dictated not only by their isoelectric points, but also by a charge dipole that may exist in the molecules due to their chimeric nature.

It will be appreciated that the CCL1 polypeptide of the present invention may comprise a single CCL1 polypeptide or alternatively may comprise two or more CCL1 polypeptides fused together according to any of the methods described hereinabove.

According to one embodiment, the CCL1 molecules are soluble under physiological conditions.

As used herein the term "soluble" refers to the ability of the molecules of the present invention to dissolve in a physiological aqueous solution (pH about 7, e.g., solubility level in aqueous media of >100 μg/ml) without substantial aggregation.

According to one embodiment, the CCL1 molecules are also selected non-immunogenic in a subject for maximizing therapeutic efficacy.

As used herein the term "non-immunogenic" refers a substance which is substantially incapable of producing an immune response in a subject administered therewith. For example, non-immunogenic in a human means that upon contacting the chimeric molecule of this aspect of the present invention with the appropriate tissue of a human, no state of sensitivity or resistance to the chimeric molecule is demonstrable upon the second administration of the chimeric molecule after an appropriate latent period (e.g., 8 to 14 days).

CCL1 of the present invention can be administered to the subject per se, or as part of a pharmaceutical composition, which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the molecule of the present invention accountable for the intended biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions fur use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purnose. More specifically, a therapeutically effective amount means an amount of active ingredients (i.e. CCL1 molecules) effective to prevent, alleviate or ameliorate symptoms of a disorder (e.g., a medical condition in which suppression of effector cells is beneficial such as autoimmune diseases and transplantation related diseases) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Examples of animal models which may be used to assess the therapeutic effective amount of CCL1 include the murine experimental autoimmune encephalomyelitis (EAE) model which serves as an experimental model for Multiple Sclerosis (MS) and other autoimmune diseases (see Example 3 of the Examples section which follows).

Toxicity and therapeutic efficacy of the active ingredients described herein can he determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

It will be appreciated that treatment of the medical conditions as mentioned above may be combined with any other method known in the art. For example, treatment of autoimmune diseases, inflammatory diseases and transplantation related diseases according to the present invention may be combined with other treatment methods known in the art (i.e., combination therapy).

Thus, for example, Multiple Sclerosis may be treated with the CCL1 polypeptide of the present invention in conjunction with other agents including, but are not limited to, Interferon Beta 1a, Interferon Beta 1b, Glatiramer Acetate, Mitoxantrone, MethylPrednisolone, Prednisone, Prednisolone, Dexamethasone, Adreno-corticotrophic Hormone (ACTH) and Corticotrophin.

Inflammatory diseases may be treated with the CCL1 polypeptide of the present invention in conjunction with other agents including, but not limited to, NSAIDs (Non-Steroidal Anti-inflammatory Drugs e.g. aspirin, ibuprofen or naproxen), corticosteroids (such as prednisone), anti-histamines, and other medications e.g. methotrexate, sulfasalazine, leflunomide, anti-TNF medications, cyclophosphamide and mycophenolate.

Transplantation related diseases (e.g. GVHD) may be treated with the CCL1 polypeptide of the present invention in conjunction with other agents including, but not limited to, immunosuppressive drugs such as CTLA4-Ig, anti-CD40 antibodies, anti-CD40 ligand antibodies, anti-B7 antibodies, anti-CD3 antibodies (for example, anti-human CD3 antibody OKT3), methotrexate (MTX), rapamycin, prednisone, methyl prednisolone, azathioprene, cyclosporin A (CsA), tacrolimus, cyclophosphamide and fludarabin, mycophenolate mofetil, daclizumab [a humanized (IgG1 Fc) anti-IL2R alpha chain (CD25) antibody], and anti-T-lymphocyte antibodies conjugated to toxins (for example, cholera A chain, or *Pseudomonas* toxin). Furthermore, the present methods may be combined with irradiation therapy or chemotherapy.

The present invention therefore contemplates articles of manufacture comprising CCL1 polypeptides and an additional agent (e.g. an anti-Multiple Sclerosis agent) being packaged in a packaging material and identified in print, in or on the packaging material for use in the treatment of the medical condition (e.g. Multiple Sclerosis).

The inventors of the present invention have shown that incubation of CD4+ Foxp3− T cells with an effective amount of CCL1 effectively induces generation of CD4+ Foxp3+ T regulatory cells (see Example 1 of the Examples section hereinbelow) and suppresses Foxp3 effector cells (see Example 4 of the Examples section hereinbelow).

Thus, according to an embodiment of the present invention, there is provided a method of suppressing effector T cells in a subject in need thereof, the method comprising administering to the subject a CCL1 polypeptide, thereby suppressing the effector T cells in the subject.

The discovery that CCL1 polarizes CD4+ Foxp3− T cells into CD4+ Foxp3+ T regulatory cells suggests the use of CCL1 for induction of CD4+ Foxp3+ T regulatory cells.

Thus, according to another aspect of the present invention there is provided a method of inducing production of CD4+ CD25+FOXp3+ T cells, the method comprising contacting a biological sample comprising CD4+ Foxp3− T cells with a CCL1 polypeptide, thereby inducing production of the CD4+CD25+FOXp3+ T cells.

The biological sample may be isolated (removed from the body) for ex-vivo or in-vitro treatment as further described hereinbelow.

As used herein, the phrase "biological sample" refers to any sample that contains T lymphocytes (e.g. CD4+ T cells, CD8+ T cells, effector T cells, regulatory T cells, etc.). Preferably, the biological sample comprises CD4+ Foxp3− T cells. The biological sample of the present invention may include a blood sample, a biopsy specimen, a biological fluid or any other tissue or cell preparation, including for example, an isolated cell population, fresh whole blood, fractionated whole blood, bone marrow, spinal fluid and/or cord blood. The cell population may be a primary cell culture or a culture adapted cell line including, but not limited to, a genetically engineered cell line, an immortalized or an immortalizable cell line, a differentiated or a differentiable cell line, a transformed cell line and the like.

The biological sample may be obtained by any method known to one of ordinary skill in the art, as for example, by a needle puncture. In cases where a cell population is used, the cells may be obtained from the subject or from a cell donor (e.g. syngeneic or non-syngeneic donor) by, for example, blood apheresis (as described in further detail below).

As used herein, the term "contacting" refers to the process of enabling direct contact of the biological sample with the CCL1 polypeptide.

According to one embodiment, contacting is effected in-vivo. Contacting in-vivo (i.e. within the body) is typically effected in a subject in need thereof (e.g. in a subject who has a medical condition in which suppression of effector T cells is beneficial).

According to another embodiment, contacting is effected ex-vivo.

Ex-vivo contacting typically refers to the process of isolating T cells (e.g. CD4+ Foxp3− T cells) from a biological sample (e.g. blood sample) and culturing them with CCL1, as for example in a culture dish or by an automated machine (e.g. cell dialysis apparatus which by automated settings separates cells from body fluids and cultures them with the appropriate substances in a sterile environment), as to enable direct contact of the cells with CCL1 polypeptide.

Thus, T cells (e.g. CD4+ Foxp3− T cells) can be isolated from an autologous origin (i.e. from the subject), from a syngeneic donor, from an allogeneic donor or from a xenogeneic donor. The T cells may also be obtained from a subject undergoing CCL1 treatment.

Furthermore, the T cells may be comprised in a crude blood sample, in PBMC, or further purified. In an exemplary embodiment, the isolated T cells are purified CD4+ Foxp3− T cells. In order to minimize the effects of graft versus host disease (GVHD), exhibited by CD8+ T cells (i.e. cytotoxic T cells), purification of CD4+ T cells, rather than CD8+ T cells is typically effected.

Several techniques are known in the art for isolating T cells [see for example, Leavitt et al., Hum. Gene Ther. 5: 1115-1120 (1994)]. The expression of surface markers facilitates identification and purification of T cells. Methods of identification and isolation of T cells include FACS, panning with magnetic beads and human T-cell subset columns. Cells isolated according to the teachings of the present invention should stay sterile and preferably maintained out of the body for a minimal time period.

Subsequent to cell isolation, the T cells are subjected to culture in the presence of CCL1. For example, the isolated T cells (about $10^4$, about $10^5$, about $10^6$, about $10^7$ or about $10^8$ cell/ml) may be cultured in the presence of rhCCL1 (about 50-1000 ng/ml, 100-1000 ng/ml, 500-1000 ng/ml, 50-500 ng/ml, 100-500 ng/ml, 100-300 ng/ml, 100-200 ng/ml, 200-500 ng/ml or 300-500 ng/ml) with or without a stimulatory peptide/activating agent (e.g. anti-CD3ε mAb and/or anti-CD28 mAb, at a concentration of about 0.1-10 μg/ml, 0.5-10 μg/ml, 1-10 μg/ml, 1-5 μg/ml, 0.5-5 μg/ml, 0.5-3 μg/ml, phorbol myristate acetate (PMA), concanavalin A (ConA) and/or MOGp35-55), in a humidified 7.5% $CO_2$ atmosphere at 37° C. for about 24-192 hours, about 48-120 hours or about 72-96 hours. Such culturing conditions enable production of CD4+ Foxp3+ T regulatory cells.

As used herein the term "T regulatory cells" or "regulatory T cells" refers to the subset of T cells, also known as suppressor T cells, which are a specialized subpopulation of T cells that act to suppress/tolerize activation of the immune system and thereby maintain immune system homeostasis and tolerance to self-antigens. CD4+ regulatory T cells may express the membrane markers CD25 and/or Foxp3.

Measuring the levels or activity of regulatory T cells can be carried out using any method known to one of ordinary skill in the art, as for example, by measuring the expression levels of CD39 on T regs (suppressory molecule, e.g. FACS analysis), by measuring the secretion levels of IL-10 (suppressory cytokine, e.g. ELISA) or by measuring the secretion levels of the enzyme granzyme (e.g. using Western Blot or ELISA assays).

According to an embodiment of the present invention, the CD4+ Foxp3− T cells (e.g. non-syngeneic cells from the donor) are cultured in the presence of irradiated cells of the subject (e.g. lymphocytes), with or without a stimulatory peptide/activating agent (as described above), in order to generate donor type CD4+ Foxp3+ T cells that suppress graft versus host disease.

According to another embodiment, the CD4+ Foxp3− T cells (e.g. syngeneic cells from the subject) are cultured in the presence of irradiated cells of the donor (e.g. lymphocytes), with or without a stimulatory peptide/activating agent (as described above), in order to generate recipient type CD4+ Foxp3+ T cells that suppress graft rejection.

In cases where the CD4+ Foxp3+ T regulatory cells are induced ex-vivo (i.e. in an isolated settings), the cells may then be administered to a subject (e.g. a subject diagnosed with a medical condition in which suppression of effector cells may be beneficial) for treatment.

Those skilled in the art are capable of determining when and how to administer the T cells to thereby treat the medical condition. The administration can be carried out via local injection, by administration into the systemic (e. g., via the blood stream or the peritoneal cavity) or portal circulation system, or by any other practical means (see for example, WO/2001/078752).

According to an embodiment of the present teachings, the CD4+ Foxp3+ T regulatory cells are specifically selected (i.e. isolated from the cell culture) prior to administering to the subject. Methods of isolating regulatory T cells are described hereinabove.

As depicted above, the T cells used for ex vivo therapy according to the present teachings may be from a non-syngeneic source (i.e. from an allogeneic or xenogeneic donor). In cases where the CD4+ Foxp3+ T regulatory cells are used for the treatment of transplantation related diseases (e.g. GVHD), the cells are typically derived from the same donor as the graft (e.g. bone marrow or solid organ).

In cases where the CD4+ Foxp3+ T regulatory cells are used for the treatment of other medical conditions, administration of purified CD4+ Foxp3+ T regulatory cells should not cause GVHD. However, in cases where there is a risk of GVHD or occurrence of GVHD, any GVHD treatment protocol may be employed. Such treatments may include administration of immunosuppressant drugs (e.g., sirolimus, tacrolimus, cyclosporine, CTLA4-Ig, anti-CD40L antibody or rapamycin) which may be administered individually or in combination. Immunosuppressant drugs may be administered prior to, concomitantly with, or following administration of the CD4+ Foxp3+ T regulatory cells.

Furthermore, administering non-syngeneic cells may cause rejection of the cells used for ex vivo therapy. Several approaches have been developed to reduce the likelihood of rejection of these non-syngeneic cells. These include either suppressing the recipient immune system (as described above) or encapsulating the non-autologous T cells in immunoisolating, semipermeable membranes prior to administration.

Encapsulation techniques are generally classified as microencapsulation, involving small spherical vehicles, and macroencapsulation, involving larger flat-sheet and hollow-fiber membranes (Uludag, H. et al. (2000). Technology of mammalian cell encapsulation. Adv Drug Deliv Rev 42, 29-64).

Methods of preparing microcapsules are known in the art and include for example those disclosed in: Lu, M. Z. et al. (2000). Cell encapsulation with alginate and alpha-phenoxycinnamylidene-acetylated poly(allylamine). Biotechnol Bioeng 70, 479-483; Chang, T. M. and Prakash, S. (2001) Procedures for microencapsulation of enzymes, cells and genetically engineered microorganisms. Mol Biotechnol 17, 249-260; and Lu, M. Z., et al. (2000). A novel cell encapsulation method using photosensitive poly(allylamine alpha-cyanocinnamylideneacetate). J Microencapsul 17, 245-521.

For example, microcapsules are prepared using modified collagen in a complex with a ter-polymer shell of 2-hydroxyethyl methylacrylate (HEMA), methacrylic acid (MAA), and methyl methacrylate (MMA), resulting in a capsule thickness of 2-5 μm. Such microcapsules can be further encapsulated with an additional 2-5 μm of ter-polymer shells in order to impart a negatively charged smooth surface and to minimize plasma protein absorption (Chia, S. M. et al. (2002). Multi-layered microcapsules for cell encapsulation. Biomaterials 23, 849-856).

Other microcapsules are based on alginate, a marine polysaccharide (Sambanis, A. (2003). Encapsulated islets in diabetes treatment. Diabetes Thechnol Ther 5, 665-668), or its derivatives. For example, microcapsules can be prepared by the polyelectrolyte complexation between the polyanions sodium alginate and sodium cellulose sulphate and the polycation poly(methylene-co-guanidine) hydrochloride in the presence of calcium chloride.

It will be appreciated that cell encapsulation is improved when smaller capsules are used. Thus, for instance, the quality control, mechanical stability, diffusion properties, and in vitro activities of encapsulated cells improved when the capsule size was reduced from 1 mm to 400 μm (Canaple, L. et al. (2002). Improving cell encapsulation through size control. J Biometer Sci Polym Ed 13, 783-96). Moreover, nanoporous biocapsules with well-controlled pore size as small as 7 nm, tailored surface chemistries, and precise microarchitectures were found to successfully immunoisolate microenvironments for cells (See: Williams, D. (1999). Small is beautiful: microparticle and nanoparticle technology in medical devices. Med Device Technol 10, 6-9; and Desai, T. A. (2002). Microfabrication technology for pancreatic cell encapsulation. Expert Opin Biol Ther 2, 633-646).

According to the present teachings, treatment of a medical condition in which suppression of effector T cells is beneficial (e.g. autoimmune disease) may be repeated as required.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi. (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

CCL1 is Involved Selection of CD4+ Foxp3+ Cells

Materials and Experimental Procedures
Mice
6-7 week-old female C57BL/6 mice were purchased from Harlan (Jerusalem, Israel) and maintained under specific pathogen-free conditions in our animal facility. All animal studies were conducted according the NIH guideline and were approved by the Technion ethics committee for experiments in animals.

Cell Purification
CD4 T cells were isolated by magnetic untouched CD4 magnetic isolation beads (Stem Cell) and then sorted by FACS Aria for GFP positive (FOXP3 positive cells) or GFP negative (for FOXP3 negative cells). The mice used were c57BL/6 mice that expressed GFP under the FOXP3 promoter.

TGF-β Induced Selection of Foxp3+ Cells
$10^6$ CD4+ T cells of naïve mice were incubated with 5 ng TGF-β (R&D), with anti-CD3/CD28 antibody (1 µg/ml), or with both anti-CD3/CD28 antibody and 5 ng TGF-β for 72 hours in DMEM stimulation medium containing different doses of goat anti-mouse CCL1 antibody (2, 8 or 30 µg, R&D).

CCL1 Induced Activation of Foxp3+ Cells
Foxp3− cells purified from spleen cells of naïve C57BL/6 mice were subjected to activation using anti-CD3/CD28 antibody (1 µg/ml, Biolegend) in cultures that were or were not supplemented with different doses of CCL1 (50 or 200 ng, R&D)

Flow Cytometry

Flow cytometry analysis was conducted according to the protocol previously described [Schif-Zuck S et al. J Immunol. (2005) 174:4307-4315].

Results

CCL1 is a CC chemokine that binds CCR8 and is its only ligand. Foxp3+ cells, preferentially, but not exclusively, express CCR8, and therefore are thought to direct the migration of these cells to sites of inflammation/graft rejection. The present inventors wanted to determine whether CCL1 is also involved in the in-vivo selection/propagation of Foxp3+ cells. To determine this, neutralizing polyclonal antibodies (Abs) to CCL1 were added to primary CD4+ T cells undergoing TGF-β induced polarization of Foxp3+ CD4+ T cells. As shown in FIGS. 1A-F, a dose dependent reduction in Foxp3+ cell selection (from 12.5 to 7.2%) was evident in the presence of anti-CCL1 antibodies. Isotype matched control antibodies displayed no effect (data not shown).

In a subsequent experiment, Foxp3− cells were purified from spleen cells of naïve C57BL/6 mice and subjected to activation using anti-CD3/CD28 antibody in cultures that were or were not supplemented with different doses of CCL1 (50 or 200 ng), without the addition of TGF-β. As shown in FIGS. 2A-C, a clear enrichment of the CD25+Foxp3+ population (from 0.92 to 2.12%) is evident in the presence of CCL1.

Taken together, these results suggest that CCL1 is involved in polarizing and potentiating Foxp3+ induced T-regs and possibly natural T-reg. Therefore, targeted neutralization of CCL1 may be useful for amplification of effector T cell reactivity whereas administration of stabilized CCL1 may further promote T-reg activities.

Example 2

CCL1-Ig Maintains the Biological Activities of CCL1

Materials and Experimental Procedures

Construction of CCL1-Ig cDNA encoding the constant region (Hinge-CH2-CH3) of mouse IgG1 Fc was generated by RT-PCR on RNA extracted from mouse spleen cells that were cultured for 4 days with LPS and IL-4. The primers used for this reaction were: sense 5' ctcgagGTGCCCAGGGATTGTGGTTG 3' (SEQ ID NO: 1) Antisense 5' gggcccTTTACCAGGAGAGTGGGAGA 3' (SEQ ID NO: 2). PCR products were digested with XhoI and ApaI and ligated into mammalian expression/secretion vector pSecTag2/Hygro B (Invitrogen Life Technologies, San Diego, Calif.), as depicted in FIG. 3A.

The following set of primers was used to generate cDNA encoding mouse CCL1 from RNA extracted from mouse Th2 cells induced by IL-4: for CCL1 inventors used 5'-CTAGCTAGCatgaaacccactgccatggca-3' (sense, SEQ ID NO: 3) and 5' CCGCTCGAGgcaggggttcaccttatcag-3' (antisense, SEQ ID NO: 4). PCR products were digested with NheI and XhoI and subcloned into the vector containing the mouse IgG1 fragment, see FIG. 3A.

Since alterations in the amino acid sequence at the N-terminus domain of a chemokine might change its properties, NheI was selected for the cloning procedure, and the original murine kappa chain leader sequence found in pSecTag2/Hygro B was replaced by mouse CCL1 leader sequence. The fused fragments were sequenced by dideoxynucleotide sequencing (Sequins version 2; Upstate Biotechnology, Cleveland, Ohio).

Expression and Purification of CCL1-Ig Fusion Protein

Expression and purification of CCL1-Ig fusion proteins was done using CHO dhfr$^{-/-}$ (DG44) cells according to the method described previously described [Carothers A M et al., Biotechniques. (1989) 7:494-496, 498-499]. The fusion protein was expressed as a disulphide-linked homodimer similar to IgG1, and had a molecular weight of approximately 85 kDa consisting of two identical 42 kDa subunits. The fusion proteins were purified from the culture medium by High-Trap protein G affinity column (BD Biosciences, Piscataway, N.J.).

Phosphorylation Assay $5\times10^6$ bw5147 thymoma cells were incubated in DMEM medium supplemented with 250 ng CCL1-Ig for 0-30 minutes or with PMA and were tested for ERK1/2 phosphorylation (Cell Signaling) by western blot analysis.

Migration Assay $10^6$ bw5147 thymoma cells were loaded in the upper chamber of a 6.5-mm diameter, 5-μm-pore polycarbonate Transwell culture-insert (Costar, Cambridge, Mass.). The lower chamber contained variable concentrations of CCL1-Ig chemokine or commercial mCCL1 (R&D). Incubation of cells was carried out at 37° C. at 7.5% CO2 for 2 hours. Migrated cells were collected and counted using a FACSCalibur (BD Biosciences).

Results

Figure 1A:
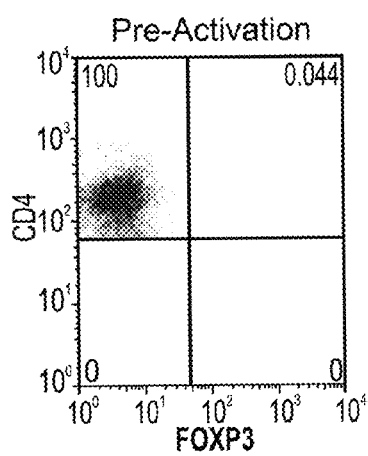
FIGS. 1A-F are dot plot graphs depicting the effect of neutralization of CCL1 on inhibition of T-reg induction by TGF-β. $10^6$ CD4+ T cells of naïve mice (FIG. 1A) were activated with anti-CD3/CD28 without TGF-β (FIG. 1B) or with 5 ng TGF-β (FIGS. 1C-F) for 72 hrs in DMEM stimulation medium. Different doses of goat anti-mouse CCL1 antibody were added to the culture medium (FIGS. 1D-F).
Figure 1B:
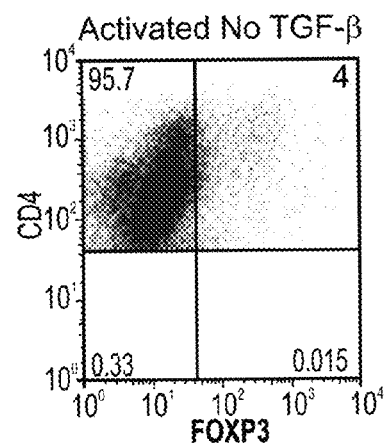
Figure 1C:
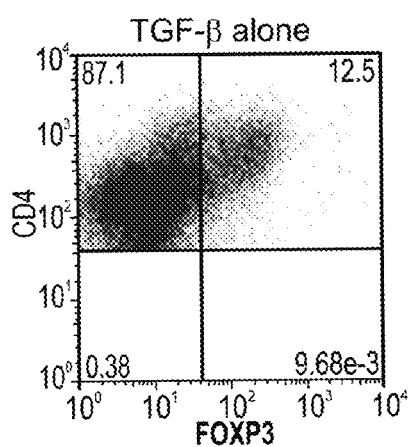
Figure 1D:
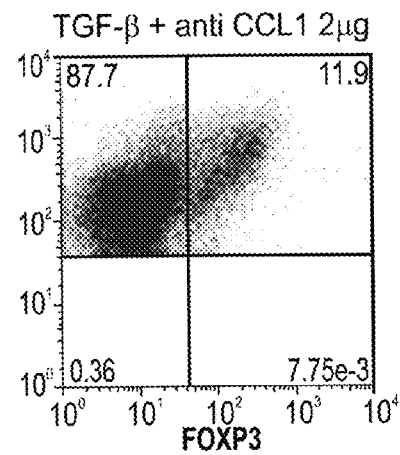
Figure 1E:
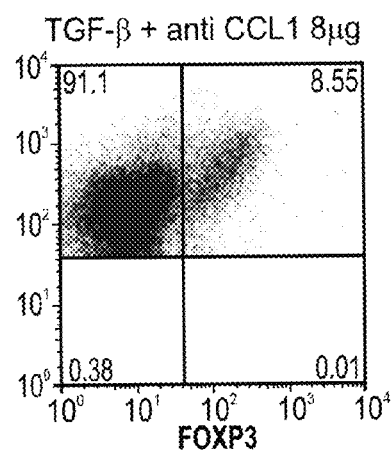
Figure 1F:
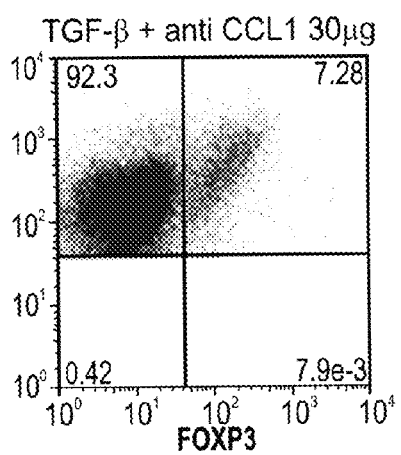
Figure 4A:
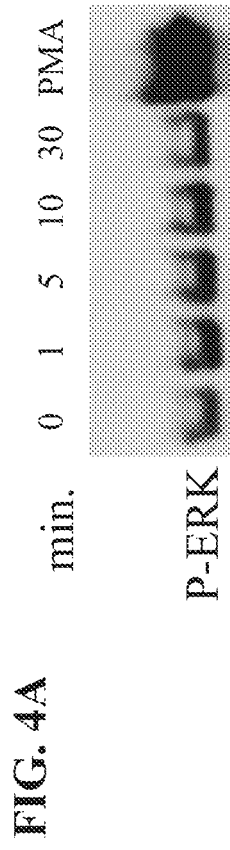
FIGS. 4A-B are pictures and graphs depicting the preserved CCL1 biological activity of CCL1-Ig.
Figure 4B:
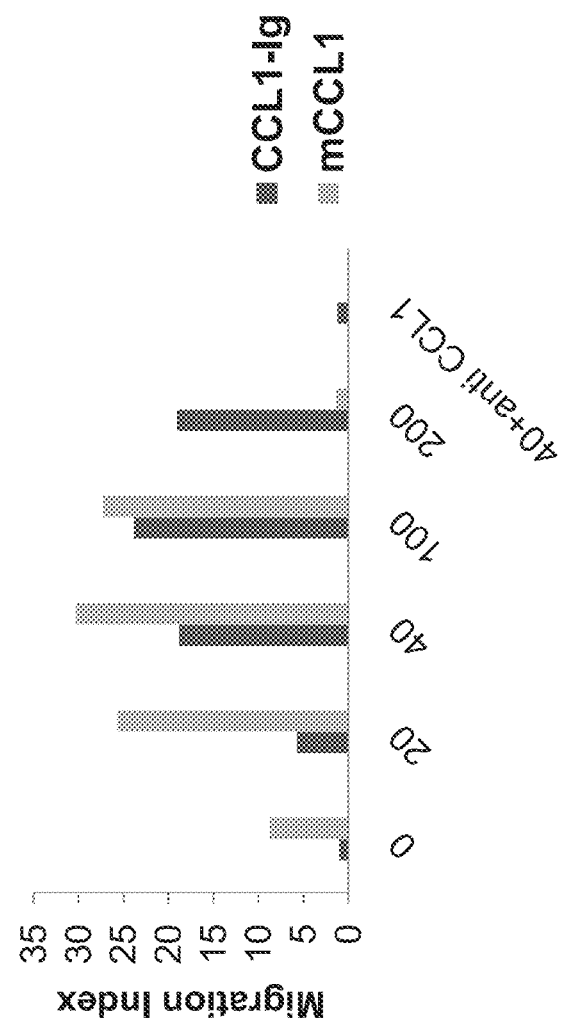

CCL1-Ig was generated as described in the materials and experimental procedures section above and schematically in FIGS. 3A-C. To verify that the recombinant fusion protein maintained the biological function of the native peptide, the present inventors first examined if it induces ERK1/2 phosphorylation as previously shown for CCL1. FIG. 4A shows that both CCL1 and CCL1-Ig induce ERK1/2 phosphorylation in the CCR8+ Bw5147 cell line. Inventors then determined the ability of both CCL1 and CCL1-Ig to induce the migration of Bw5147 cells. FIG. 4B shows that both peptides are highly potent inducers of cell migration that could be neutralized by anti-CCL1 neutralizing Abs (R&D).

Example 3

Administration of CCL1-Ig Suppresses Ongoing EAE

Materials and Experimental Procedures

Mice

See Example 1, above.

Peptides

Myelin Oligodendrocyte Glycoprotein $MOG_{p35-55}$ was previously constructed. After purification by HPLC, the sequence was confirmed by amino acid analysis, and the correct mass was checked by mass spectroscopy. Purification of the peptide that was used in the current study was more than 95%.

Induction of Active EAE

EAE was induced by immunizing mice with $MOG_{p35-55}$/CFA, as previously described [Tompkins S M et al., J Immunol. (2002) 168:4173-4183]. Briefly, 6-7 week old female C57BL/6 mice were immunized s.c. with 200 μl of an emulsion containing 800 μg M. tuberculosis H37Ra and 200 μg $MOG_{p35-55}$. Animals were then monitored daily for clinical signs by an observer blind to the treatment protocol. EAE scoring: 0, clinically normal; 1, flaccid tail; 2, hind limb paralysis; 3, Total hind limb paralysis, accompanied by an apparent front limb paralysis; 4, Total hind limb and front limb paralysis.

Construction of CCL1-Ig
See Example 2, above.
Expression and Purification of CCL1-Ig Fusion Protein
See Example 2, above.
Results
FIGS. 5A-B summarize the results of two independent experiments testing the effect of CCL1-Ig on EAE. CCL1C57BL/6 female mice (n=6 per group) were subjected to active induction of $MOG_{p35-55}$-induced EAE, and at the onset of disease (day 12) were separated into two equally sick groups (n=6 mice per group). For the first experiment, mice were injected i.p. either with PBS control or 300 μg/mouse of mCCL1-Ig on days 13, 15, 17 and 19 after the induction of disease (FIG. 5A). For the second experiment, mice were injected i.p. either with PBS control, 300 μg/mouse of mCCL1-Ig or IgG on days 12, 14, 16 and 18 after the induction of disease (FIG. 5B). An observer blind to the experimental protocol monitored the development and progression of disease. The results (n=6 mice per each group) are shown as the mean maximal score±SE. The arrow indicates the first day of mCCL1-Ig administration. As shown in FIGS. 5A-B, mice treated with CCL1-Ig exhibited rapid recovery from the disease (FIG. 5A, Day 20 mean maximal score 2.0±0.33 vs 1±0.166, P<0.01). Treatment with isotype matched IgG did not have a significant effect (FIG. 5B).

Taken together, these results illustrate that CCL1-Ig displays an essential role in directing the transformation of Foxp3− CD4+ T cells into Foxp3+ CD4+ T cells (i-Tregs) and in suppressing the progression of autoimmune EAE disease.

Example 4

CCL1 Suppresses Foxp3 Effector Cells

Materials and Experimental Procedures
Treg Suppression Assay
CD4+CD25+FOXP3− T cells (T eff) were incubated with or without CD4+CD25+FOXP3+ T cells (T reg) in the presence of CCL1 (250 ng, R&D), anti-CCL1 (5 μg/ml, R&D), CCL2 (250 ng, R&D) or with medium alone. Cells were activated with anti-CD3/CD28 antibody (1 μg/ml) and APCs (CD11c isolated cells) for 3 days. Proliferation was measured by thymidine (3H) uptake during the last 16 hours of incubation and radiation levels were represented as cpm (counts per minute).
Results
To gain insight regarding the mechanistic basis of how CCL1 affects the biological function of Foxp3+ T cells, this chemokine was evaluated for its ability to induce suppression of Foxp3 effector T cell proliferation in a mixed lymphocyte reaction. As shown in FIG. 6, a significant reduction (42%) in the proliferation rate of effector cells was measured when Foxp3+ T cells were cultured in the presence of CCL1 (p<0.001).

Example 5

CCL1 Induces CD4 T Regulatory Cells in a Graft Versus Host Disease (GVHD) Model

Materials and Experimental Procedures
Cells
CD4+ T cells from C57BL/6 mice expressing GFP under the FOXp3 promoter (C57b6—FOXP3 GFP) were incubated with non CD4 Balb/c splenocytes for 7 days, in the presence of CCL1, CCL21 or TGF-β, and measured for the ability to induce FOXP3 T regulatory cells (Treg).
Bi-Directional Mixed Lymphocyte Reaction
CD4+ T cells from C57BL/6 mice expressing GFP under the FOXp3 promoter (C57b6—FOXP3 GFP) were incubated with non CD4 Balb/c splenocytes for 7 days in the presence of CCL1 (10-250 ng/ml, R&D), CCL21 (250 ng/ml, R&D) or TGF-β (2 ng/ml, R&D) and measured for the ability to induce FOXP3 T regulatory cells (Treg). TGF-β was used as a positive control while CCL21 was used as a negative control.
Flow Cytometry
See Example 1, above.
Results
Graft-versus-host disease (GVHD) is a major obstacle in allogeneic hematopoietic cell transplantation. In GVHD, residual T cells of the host attack the graft (transplanted bone marrow), but importantly, also CD4+ T cells from the donor (graft) attack the host, resulting in graft versus host inflammatory process.

The present inventors utilized a bi-directional mixed lymphocyte reaction (MLR) assay as an in-vitro model for GVHD. In the present bi-directional MLR assay, CD4+ T cells from C57BL/6 mice expressing GFP under the FOXp3 promoter (C57b6—FOXP3 GFP) were incubated with non CD4 Balb/c splenocytes for 7 days, in the presence of CCL1, CCL21 or TGF-β, and measured for the ability to induce FOXP3 T regulatory cells (Treg). The present results (FIGS. 7A-F) clearly demonstrate that addition of CCL1 to the cell culture significantly increased the polarization of FOXp3+ T-regs in a dose dependent manner (from 0.27% to 16.8%, FIGS. 7A-D) in a similar manner as the positive control (TGF-β, FIG. 7E).

Example 6

Treatment of TNBS Induced IBD by CCL1-Ig, Presenting the Effectiveness of CCl1-Ig in Treating Inflammatory Bowel Disease (IBD)

Objectives
The objective of the study presented in this example was to assess potential efficacy of CCL1-Ig administrated to mice by a repeated IP treatment.

Study End Points

Measurements of:
Survival
Weight loss
Inflammatory bowel disease (IBD) typical clinical studies (Wallace score)
Histological evaluation (scoring)
Experimental Protocol
Mice
SJL 6-7 weeks of age male mice were purchased from Harlan Laboratories, Israel.
Environment Conditions:
Animals were housed under SPF laboratory conditions, in IVC cage system with adequate fresh air supply. Animals were kept in a climate-controlled environment. Temperatures range was between 20-24° C. and the relative humidity was between 30-70%, with 12 hours light and 12 hours dark cycles.

Randomization

Animals were randomized and divided into four groups, seven mice in each group.

Experimental Design and Conditions

Dosing

IBD was induced by the administration of 0.1 ml of trinitrobenzenesulfonic acid (TNBS, 1% in 50% ethanol) to mice that fasted for 24 hours (access to water was not interrupted). The final amount that was administered was calculated to be 3 mg/Kg body weight. A dose of 300 μg CCL1-Ig was injected (i.p.) 24 h after the clinical onset of disease, followed by three times a week (every other day except Saturday). Control mice were administered with phosphate buffered saline (PBS), or with isotype matched control IgG (not shown).

Tests and Evaluation:

Body weight: Body weight was measured on study day 0 and daily up to study termination (seven days).

Clinical signs: The animals were observed for clinical signs and stool condition daily.

Termination & Necropsy

At study termination, the animals were sacrificed by carbon dioxide asphyxiation. Colons were harvested at the experimental end-point (day 7), scored according to Wallace score (Wallace et. al. 1996. J. Clin. Invest. 98, 2076-2085). After the length of the colons was measured they were fixed in formalin and subjected to histological evaluation.

Statistical Analyses

One-way ANOVA Kruskal-Wallis test with multiple comparisons was used to analyze the data. A value of $P<0.05$ was considered significant.

Results & Conclusions

CCL1 Ameliorates TNBS Induced Colitis in SJL Mice.

Figures 8A, 8B:
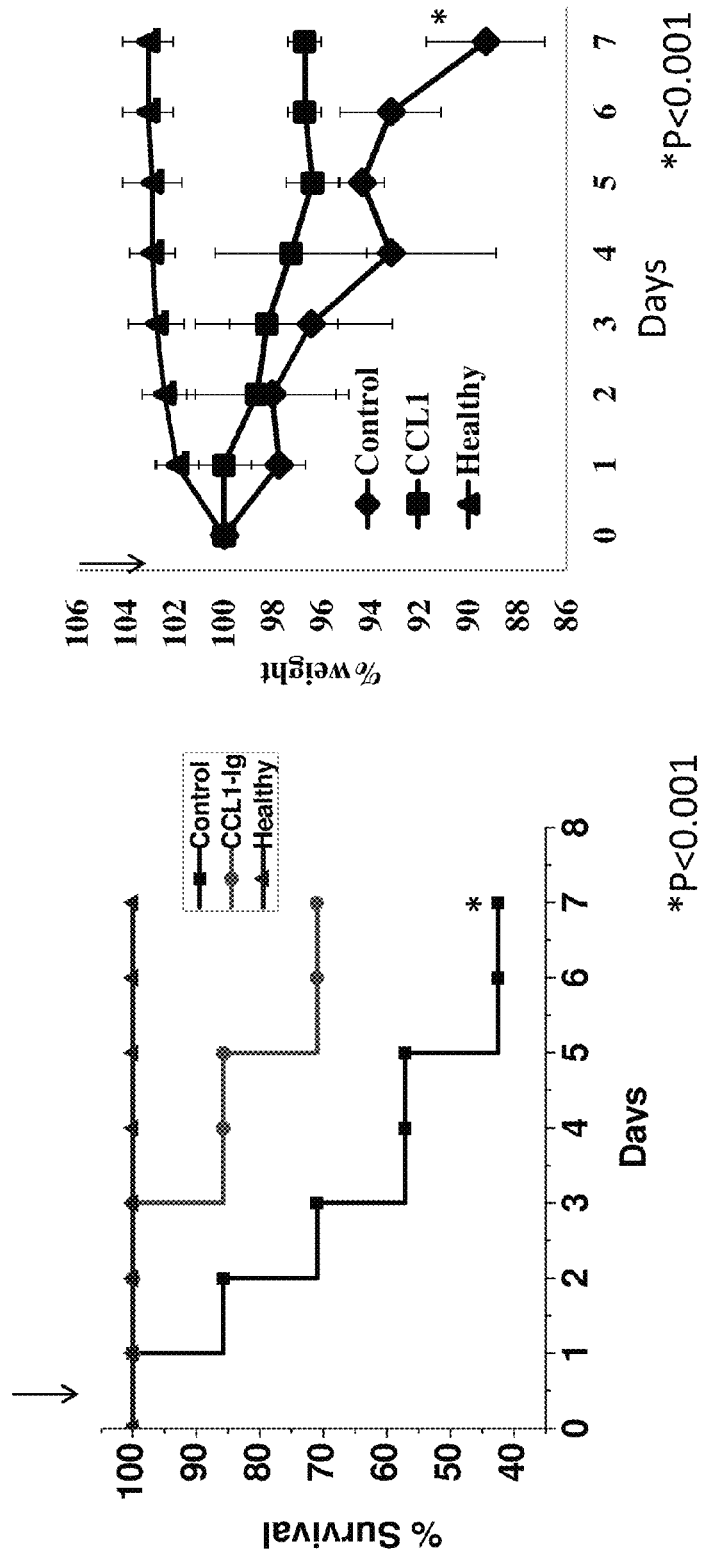
FIG. 8A presents the survival percentage of three groups of mice over a course of seven days, wherein the three groups include a control, healthy mice and mice treated with CCl1-Ig.
FIG. 8B presents the body weight loss over a course of seven days for the same three groups of mice.

As detailed above, IBD was induced in 24 hr starved SJL mice using TNBS/50% Ethanol colonic enema. In the first day after induction of disease the mice (seven per group) were injected daily either by PBS or by CCL1-Ig (300 μg). The mice were monitored for survival (FIG. 8A) and weight on a daily basis (FIG. 8B). Survival and weight curves showing the progress of disease in either group. Particularly, FIG. 8 shows that the repeated administration of CCL1-Ig prevented mortality (FIG. 8A, 40% .vs. 70%, $p<0.01$) and body weight loss (FIG. 8B 4% .vs. 18% in seven days, $p<0.01$). The administration of isotype matched IgG had no effect compared to PBS (not shown).

Macroscopic Assessment of TNBS Induced IBD.

As detailed above, Control and CCL1-Ig treated mice were sacrificed and complete colons were removed. The colons were analyzed macroscopically for length, ulcers and necrosis of tissue. The scores were given according to Table I below.

TABLE I

Macroscopic assessment of colonic damage

| Macroscopic damage | Score |
|---|---|
| No damage | 0 |
| Hyperemia but no ulcers | 1 |
| Fibrosis but no ulcers | 2 |
| Ulceration necrosis <1 cm | 3 |
| Ulceration necrosis <2 cm | 4 |
| Ulceration necrosis >2 cm | 5 |

FIG. 9A shows that CCL1-Ig based therapy partially reconstituted colon length (7.4±0.4 compared to 6.6±0.4, $p<0.05$). FIG. 9B shows that CCl1-Ig based therapy provides a reduced macroscopic score (Wallach Score) (2±0.4 compared to 4±0.3, $p<0.01$).

Histological Results

As detailed above, Control and CCL1-Ig treated mice were sacrificed and complete colons were removed. The colons were paraffin embedded and stained for H&E stain and microscopically analyzed by the scores presented in Table II below. The data represents seven mice per group and 15 slides per colon.

TABLE II microscopic assessment of colonic inflammations

| Histological appearance | Score |
|---|---|
| Extent of ulceration | |
| No ulcers | 0 |
| Small ulcers (<3 mm) | 1-2 |
| Large ulcers (>3 mm) | 3-5 |
| Submucosal infiltration | |
| None | 0 |
| Mild | 1 |
| Moderate | 2-3 |
| Severe | 4-5 |
| Crypt abscesses | |
| None | 0 |
| Rare | 1-2 |
| Diffuse | 3-5 |
| Wall thickness (μm) | |
| <470 | 0 |
| <600 | 1 |
| <700 | 2 |
| <800 | 3 |
| <900 | 4 |
| >900 | 5 |

Figures 10A, 10B:
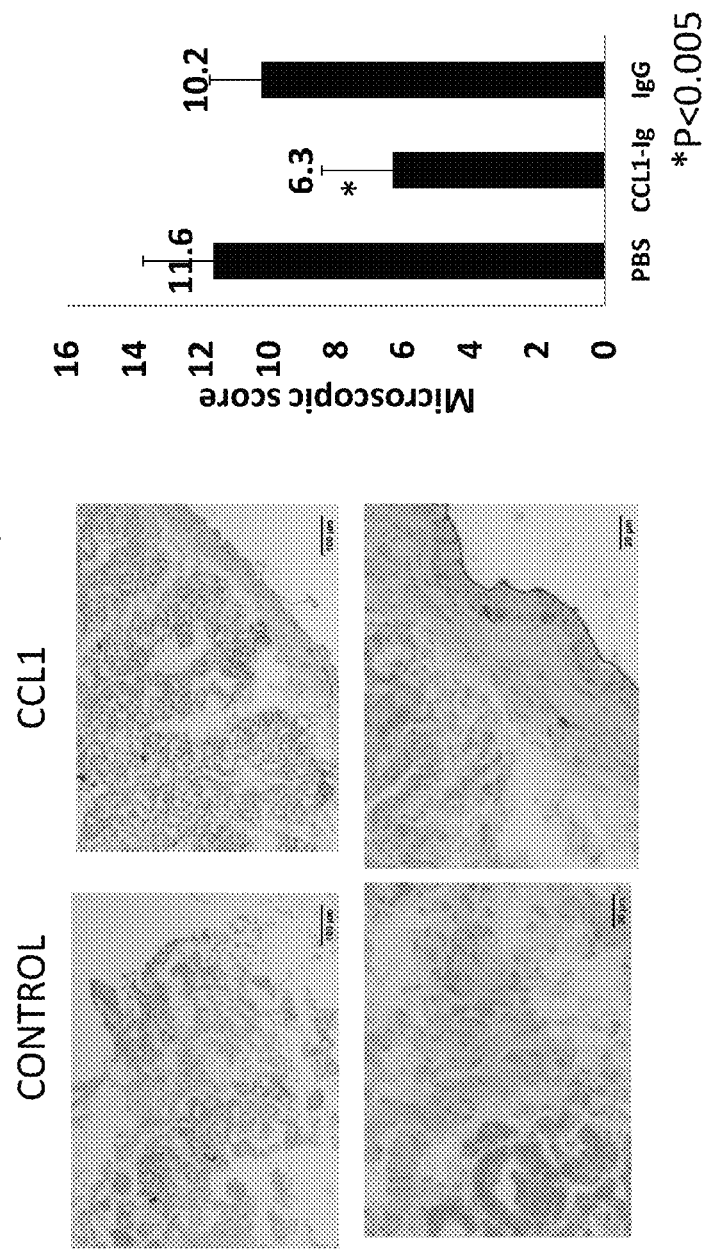
FIGS. 10A and 10B present a histological analysis of the colons of control and CCl1-Ig treated mice (FIG. 10A) and the microscopic assessment of colon inflammation (FIG. 10B).

As presented in FIGS. 10A and 10B, the histological analyses showed a significant reduction in microscopic scores in these mice (FIG. 10, 6.3±0.4 compared to 11.6±0.5, $p<0.005$). Collectively the data clearly shows that CCL1-Ig could be used for therapy of IBD.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating an inflammatory bowel disease (IBD) in a subject in need thereof, the method comprising administering to the subject a therapeutically effective amount of a CCL1 fusion polypeptide comprising SEQ NO: 8 and an Fc constant region of an immunoglobulin, thereby treating the IBD in the subject in need thereof.

2. The method of claim 1, wherein said CCL1 fusion polypeptide is as set forth in SEQ ID NO: 10.

3. The method of claim 1, wherein the IBD is selected from group consisting of colitis and Crohn's disease.

* * * * *

SEQUENCE LISTING

<160> NUMBER OF SEQ ID NOS: 16

<210> SEQ ID NO 1
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 1
ctcgaggtgc ccagggattg tggttg                                          26

<210> SEQ ID NO 2
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 2
gggcccttta ccaggagagt gggaga                                          26

<210> SEQ ID NO 3
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 3
ctagctagca tgaaacccac tgccatggca                                      30

<210> SEQ ID NO 4
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 4
ccgctcgagg caggggttca ccttcttcag                                      30

<210> SEQ ID NO 5
<211> LENGTH: 693
<212> TYPE: DNA
<213> ORGANISM: Artificial sequence
<220> FEATURE:
<223> OTHER INFORMATION: Human IgG constant region (Fc) coding sequence

<400> SEQUENCE: 5
cccaaatctt gtgacaaaac tcacacatgc ccaccgtgcc cagcacctga actcctgggg      60
ggaccgtcag tcttcctctt ccccccaaaa cccaaggaca ccctcatgat ctcccggacc     120
cctgaggtca catgcgtggt ggtggacgtg agccacgaag accctgaggt caagttcaac     180
tggtacgtgg acggcgtgga ggtgcataat gccaagacaa agccgcggga ggagcagtac     240
aacagcacgt accgtgtggt cagcgtcctc accgtcctgc accaggactg gctgaatggc     300
aaggagtaca agtgcaaggt ctccaacaaa gccctcccag cccccatcga gaaaaccatc     360
tccaaagcca agggcagcc cgagaacca caggtgtaca ccctgccccc atcccgggag      420
gagatgacca agaaccaggt cagcctgacc tgcctggtca aaggcttcta tcccagcgac     480
atcgccgtgg agtgggagag caatgggcag ccggagaaca actacaagac cacgcctccc     540
gtgctggact ccgacggctc cttcttcctc tatagcaagc tcaccgtgga caagagcagg     600

| | | |
|---|---|---|
| tggcagcagg ggaacgtctt ctcatgctcc gtgatgcatg aggctctgca caaccactac | 660 |
| acgcagaaga gcctctccct gtccccgggt aaa | 693 |

<210> SEQ ID NO 6
<211> LENGTH: 231
<212> TYPE: PRT
<213> ORGANISM: Artificial sequence
<220> FEATURE:
<223> OTHER INFORMATION: Human IgG constant region (Fc)

<400> SEQUENCE: 6

```
Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 7
<211> LENGTH: 291
<212> TYPE: DNA
<213> ORGANISM: Artificial sequence
<220> FEATURE:
<223> OTHER INFORMATION: Human CCL1 coding sequence

<400> SEQUENCE: 7

| | | |
|---|---|---|
| atgcagatca tcaccacagc cctggtgtgc ttgctgctag ctgggatgtg gccggaagat | 60 |
| gtggacagca agagcatgca ggtacccttc tccagatgtt gcttctcatt tgcggagcaa | 120 |
| agagattccc tgagggcaat cctgtgttac agaaatacca gctccatctg ctccaatgag | 180 |
| ggcttaatat tcaagctgaa gagaggcaaa gaggcctgcg ccttgacac agttggatgg | 240 |
| gttcagaggc acagaaaaat gctgaggcac tgcccgtcaa aagaaaatg a | 291 |

<210> SEQ ID NO 8
<211> LENGTH: 96
<212> TYPE: PRT
<213> ORGANISM: Artificial sequence
<220> FEATURE:
<223> OTHER INFORMATION: Human CCL1

<400> SEQUENCE: 8

```
Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
            20                  25                  30

Cys Cys Phe Ser Phe Ala Glu Gln Glu Ile Pro Leu Arg Ala Ile Leu
        35                  40                  45

Cys Tyr Arg Asn Thr Ser Ser Ile Cys Ser Asn Glu Gly Leu Ile Phe
    50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95
```

<210> SEQ ID NO 9
<211> LENGTH: 984
<212> TYPE: DNA
<213> ORGANISM: Artificial sequence
<220> FEATURE:
<223> OTHER INFORMATION: Human CCL1-IgG fusion protein coding sequence

<400> SEQUENCE: 9

| | | | | | |
|---|---|---|---|---|---|
| atgcagatca | tcaccacagc | cctggtgtgc | ttgctgctag | ctgggatgtg | gccggaagat | 60 |
| gtggacagca | agagcatgca | ggtacccttc | tccagatgtt | gcttctcatt | tgcggagcaa | 120 |
| gagattcccc | tgagggcaat | cctgtgttac | agaaatacca | gctccatctg | ctccaatgag | 180 |
| ggcttaatat | tcaagctgaa | gagaggcaaa | gaggcctgcg | ccttggacac | agttggatgg | 240 |
| gttcagaggc | acagaaaaat | gctgaggcac | tgcccgtcaa | aagaaaatg | acccaaatct | 300 |
| tgtgacaaaa | ctcacacatg | cccaccgtgc | ccagcacctg | aactcctggg | gggaccgtca | 360 |
| gtcttcctct | tccccccaaa | acccaaggac | accctcatga | tctcccggac | ccctgaggtc | 420 |
| acatgcgtgg | tggtggacgt | gagccacgaa | gaccctgagg | tcaagttcaa | ctggtacgtg | 480 |
| gacggcgtgg | aggtgcataa | tgccaagaca | aagccgcggg | aggagcagta | caacagcacg | 540 |
| taccgtgtgg | tcagcgtcct | caccgtcctg | caccaggact | ggctgaatgg | caaggagtac | 600 |
| aagtgcaagg | tctccaacaa | agccctccca | gcccccatcg | agaaaaccat | ctccaaagcc | 660 |
| aaagggcagc | cccgagaacc | acaggtgtac | accctgcccc | catcccggga | ggagatgacc | 720 |
| aagaaccagg | tcagcctgac | ctgcctggtc | aaaggcttct | atcccagcga | catcgccgtg | 780 |
| gagtgggaga | gcaatgggca | gccggagaac | aactacaaga | ccacgcctcc | cgtgctggac | 840 |
| tccgacggct | ccttcttcct | ctatagcaag | ctcaccgtgg | acaagagcag | gtggcagcag | 900 |
| gggaacgtct | tctcatgctc | cgtgatgcat | gaggctctgc | acaaccacta | cacgcagaag | 960 |
| agcctctccc | tgtccccggg | taaa | | | | 984 |

<210> SEQ ID NO 10
<211> LENGTH: 327
<212> TYPE: PRT
<213> ORGANISM: Artificial sequence
<220> FEATURE:
<223> OTHER INFORMATION: Human CCL1-IgG fusion protein coding sequence

```
<400> SEQUENCE: 10

Met Gln Ile Ile Thr Thr Ala Leu Val Cys Leu Leu Leu Ala Gly Met
1               5                   10                  15

Trp Pro Glu Asp Val Asp Ser Lys Ser Met Gln Val Pro Phe Ser Arg
            20                  25                  30

Cys Cys Phe Ser Phe Ala Glu Gln Glu Ile Pro Leu Arg Ala Ile Leu
        35                  40                  45

Cys Tyr Arg Asn Thr Ser Ser Ile Cys Ser Asn Glu Gly Leu Ile Phe
    50                  55                  60

Lys Leu Lys Arg Gly Lys Glu Ala Cys Ala Leu Asp Thr Val Gly Trp
65                  70                  75                  80

Val Gln Arg His Arg Lys Met Leu Arg His Cys Pro Ser Lys Arg Lys
                85                  90                  95

Pro Lys Ser Cys Asp Lys Thr His Thr Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 11
<211> LENGTH: 681
<212> TYPE: DNA
<213> ORGANISM: Artificial sequence
<220> FEATURE:
<223> OTHER INFORMATION: Mouse IgG constant region coding sequence

<400> SEQUENCE: 11
gtgcccaggg attgtggttg taagccttgc atatgtacag tcccagaagt atcatctgtc      60
ttcatcttcc ccccaaagcc caaggatgtg ctcaccatta ctctgactcc taaggtcacg     120
```

```
tgtgttgtgg tagacatcag caaggatgat cccgaggtcc agttcagctg gtttgtagat    180
gatgtggagg tgcacacagc tcagacgcaa ccccgggagg agcagttcaa cagcactttc    240
cgctcagtca gtgaacttcc catcatgcac caggactgcc tcaatggcaa ggagttcaaa    300
tgcagggtca acagtgcagc tttccctgcc cccatcgaga aaccatctc caaaaccaaa     360 ggcagaccga aggctccaca ggtgtacacc attccacctc ccaaggagca gatggccaag    420
gataaagtca gtctgacctg catgataaca gacttcttcc ctgaagacat tactgtggag    480
tggcagtgga atgggcagcc agcggagaac tacaagaaca ctcagcccat catggacaca    540
gatggctctt acttcgtcta cagcaagctc aatgtgcaga gagcaactg ggaggcagga     600 aatactttca cctgctctgt gttacatgag ggcctgcaca accaccatac tgagaagagc    660
ctctcccact ctcctggtaa a                                               681
```

<210> SEQ ID NO 12
<211> LENGTH: 227
<212> TYPE: PRT
<213> ORGANISM: Artificial sequence
<220> FEATURE:
<223> OTHER INFORMATION: Mouse IgG constant region

<400> SEQUENCE: 12

```
Val Pro Arg Asp Cys Gly Cys Lys Pro Cys Ile Cys Thr Val Pro Glu
1               5                   10                  15

Val Ser Ser Val Phe Ile Phe Pro Pro Lys Pro Lys Asp Val Leu Thr
            20                  25                  30

Ile Thr Leu Thr Pro Lys Val Thr Cys Val Val Val Asp Ile Ser Lys
        35                  40                  45

Asp Asp Pro Glu Val Gln Phe Ser Trp Phe Val Asp Asp Val Glu Val
    50                  55                  60

His Thr Ala Gln Thr Gln Pro Arg Glu Glu Gln Phe Asn Ser Thr Phe
65                  70                  75                  80

Arg Ser Val Ser Glu Leu Pro Ile Met His Gln Asp Cys Leu Asn Gly
                85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
        115                 120                 125

Tyr Thr Ile Pro Pro Pro Lys Glu Gln Met Ala Lys Asp Lys Val Ser
    130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
            180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
    210                 215                 220

Pro Gly Lys
225
```

```
<210> SEQ ID NO 13
<211> LENGTH: 279
<212> TYPE: DNA
<213> ORGANISM: Artificial sequence
<220> FEATURE:
<223> OTHER INFORMATION: Mouse CCL1 coding sequence

<400> SEQUENCE: 13
atgaaaccca ctgccatggc actgatgtgc ctgctgctgg ctgccgtgtg gatacaggat      60
gttgacagca agagcatgct tacggtctcc aatagctgct gcttgaacac cttgaagaaa     120
gagcttcccc tgaagtttat ccagtgttac agaaagatgg ctcctcctg tcctgatccc     180 ccagctgtgg tattcaggct gaacaaaggt agagaaagct gcgcctcaac taacaaaacg     240
tgggttcaaa atcacctgaa gaaggtgaac cctgctaa                             279

<210> SEQ ID NO 14
<211> LENGTH: 92
<212> TYPE: PRT
<213> ORGANISM: Artificial sequence
<220> FEATURE:
<223> OTHER INFORMATION: Mouse CCL1

<400> SEQUENCE: 14

Met Lys Pro Thr Ala Met Ala Leu Met Cys Leu Leu Leu Ala Ala Val
1               5                   10                  15

Trp Ile Gln Asp Val Asp Ser Lys Ser Met Leu Thr Val Ser Asn Ser
            20                  25                  30

Cys Cys Leu Asn Thr Leu Lys Lys Glu Leu Pro Leu Lys Phe Ile Gln
        35                  40                  45

Cys Tyr Arg Lys Met Gly Ser Ser Cys Pro Asp Pro Pro Ala Val Val
    50                  55                  60

Phe Arg Leu Asn Lys Gly Arg Glu Ser Cys Ala Ser Thr Asn Lys Thr
65                  70                  75                  80

Trp Val Gln Asn His Leu Lys Lys Val Asn Pro Cys
                85                  90

<210> SEQ ID NO 15
<211> LENGTH: 960
<212> TYPE: DNA
<213> ORGANISM: Artificial sequence
<220> FEATURE:
<223> OTHER INFORMATION: Mouse CCL1-IgG fusion protein coding sequence

<400> SEQUENCE: 15
atgaaaccca ctgccatggc actgatgtgc ctgctgctgg ctgccgtgtg gatacaggat      60
gttgacagca agagcatgct tacggtctcc aatagctgct gcttgaacac cttgaagaaa     120
gagcttcccc tgaagtttat ccagtgttac agaaagatgg ctcctcctg tcctgatccc     180 ccagctgtgg tattcaggct gaacaaaggt agagaaagct gcgcctcaac taacaaaacg     240
tgggttcaaa atcacctgaa gaaggtgaac cctgctaag tgcccaggga ttgtggttgt     300
aagccttgca tatgtacagt cccagaagta tcatctgtct tcatcttccc cccaaagccc     360
aaggatgtgc tcaccattac tctgactcct aaggtcacgt gtgttgtggt agacatcagc     420
aaggatgatc ccgaggtcca gttcagctgg tttgtagatg atgtggaggt gcacacagct     480
cagacgcaac cccgggagga gcagttcaac agcactttcc gctcagtcag tgaacttccc     540
atcatgcacc aggactgcct caatggcaag gagttcaaat gcagggtcaa cagtgcagct     600
ttccctgccc ccatcgagaa aaccatctcc aaaaccaaag gcagaccgaa ggctccacag     660
```

```
gtgtacacca ttccacctcc caaggagcag atggccaagg ataaagtcag tctgacctgc    720
atgataacag acttcttccc tgaagacatt actgtggagt ggcagtggaa tgggcagcca    780
gcggagaact acaagaacac tcagcccatc atggacacag atggctctta cttcgtctac    840
agcaagctca atgtgcagaa gagcaactgg gaggcaggaa atactttcac ctgctctgtg    900
ttacatgagg cctgcacaa ccaccatact gagaagagcc tctcccactc tcctggtaaa    960
```

<210> SEQ ID NO 16
<211> LENGTH: 319
<212> TYPE: PRT
<213> ORGANISM: Artificial sequence
<220> FEATURE:
<223> OTHER INFORMATION: Mouse CCL1-IgG fusion protein

<400> SEQUENCE: 16

```
Met Lys Pro Thr Ala Met Ala Leu Met Cys Leu Leu Ala Ala Val
1               5                   10                  15

Trp Ile Gln Asp Val Asp Ser Lys Ser Met Leu Thr Val Ser Asn Ser
            20                  25                  30

Cys Cys Leu Asn Thr Leu Lys Lys Glu Leu Pro Leu Lys Phe Ile Gln
        35                  40                  45

Cys Tyr Arg Lys Met Gly Ser Ser Cys Pro Asp Pro Ala Val Val
    50                  55                  60

Phe Arg Leu Asn Lys Gly Arg Glu Ser Cys Ala Ser Thr Asn Lys Thr
65                  70                  75                  80

Trp Val Gln Asn His Leu Lys Lys Val Asn Pro Cys Val Pro Arg Asp
                85                  90                  95

Cys Gly Cys Lys Pro Cys Ile Cys Thr Val Pro Glu Val Ser Ser Val
            100                 105                 110

Phe Ile Phe Pro Pro Lys Pro Lys Asp Val Leu Thr Ile Thr Leu Thr
        115                 120                 125

Pro Lys Val Thr Cys Val Val Val Asp Ile Ser Lys Asp Asp Pro Glu
    130                 135                 140

Val Gln Phe Ser Trp Phe Val Asp Asp Val Glu Val His Thr Ala Gln
145                 150                 155                 160

Thr Gln Pro Arg Glu Glu Gln Phe Asn Ser Thr Phe Arg Ser Val Ser
                165                 170                 175

Glu Leu Pro Ile Met His Gln Asp Cys Leu Asn Gly Lys Glu Phe Lys
            180                 185                 190

Cys Arg Val Asn Ser Ala Ala Phe Pro Ala Pro Ile Glu Lys Thr Ile
        195                 200                 205

Ser Lys Thr Lys Gly Arg Pro Lys Ala Pro Gln Val Tyr Thr Ile Pro
    210                 215                 220

Pro Pro Lys Glu Gln Met Ala Lys Asp Lys Val Ser Leu Thr Cys Met
225                 230                 235                 240

Ile Thr Asp Phe Phe Pro Glu Asp Ile Thr Val Glu Trp Gln Trp Asn
                245                 250                 255

Gly Gln Pro Ala Glu Asn Tyr Lys Asn Thr Gln Pro Ile Met Asp Thr
            260                 265                 270

Asp Gly Ser Tyr Phe Val Tyr Ser Lys Leu Asn Val Gln Lys Ser Asn
        275                 280                 285
```

-continued

```
Trp Glu Ala Gly Asn Thr Phe Thr Cys Ser Val Leu His Glu Gly Leu
    290                 295                 300

His Asn His His Thr Glu Lys Ser Leu Ser His Ser Pro Gly Lys
305             310                 315
```